(12) United States Patent
Ali et al.

(10) Patent No.: US 12,344,616 B2
(45) Date of Patent: Jul. 1, 2025

(54) FACTOR XIa INHIBITORS

(71) Applicant: Merck Sharp & Dohme LLC, Rahway, NJ (US)

(72) Inventors: Amjad Ali, Freehold, NJ (US); John S. Debenham, Scotch Plains, NJ (US); Cheng Zhu, Edison, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 547 days.

(21) Appl. No.: 17/286,525

(22) PCT Filed: Oct. 21, 2019

(86) PCT No.: PCT/US2019/057119
§ 371 (c)(1),
(2) Date: Apr. 19, 2021

(87) PCT Pub. No.: WO2020/086416
PCT Pub. Date: Apr. 30, 2020

(65) Prior Publication Data
US 2021/0355131 A1  Nov. 18, 2021

Related U.S. Application Data

(60) Provisional application No. 62/750,474, filed on Oct. 25, 2018.

(51) Int. Cl.
*C07D 487/08* (2006.01)
(52) U.S. Cl.
CPC .................. *C07D 487/08* (2013.01)
(58) Field of Classification Search
CPC .......... C07D 487/08; A61K 45/06; A61P 7/02
See application file for complete search history.

(56) References Cited

U.S. PATENT DOCUMENTS 9,453,018 B2   9/2016   Dilger et al.

FOREIGN PATENT DOCUMENTS

| WO | 2015123090 A1 | 8/2015 |
| WO | 2017074832 A1 | 5/2017 |
| WO | 2017074833 A1 | 5/2017 |

OTHER PUBLICATIONS

Al-Horani Expert Opinion on Therapeutic Patents, 26, 3, 323-345 (Year: 2016).*

* cited by examiner

*Primary Examiner* — Umamaheswari Ramachandran
(74) *Attorney, Agent, or Firm* — Daniel Woods; John C. Todaro

(57) ABSTRACT

The present invention provides a compound of Formula (I) and pharmaceutical compositions comprising one or more said compounds, and methods for using said compounds for treating or preventing thromboses, embolisms, hypercoagulability or fibrotic changes. The compounds are selective Factor XIa inhibitors or dual inhibitors of Factor XIa and plasma kallikrein.

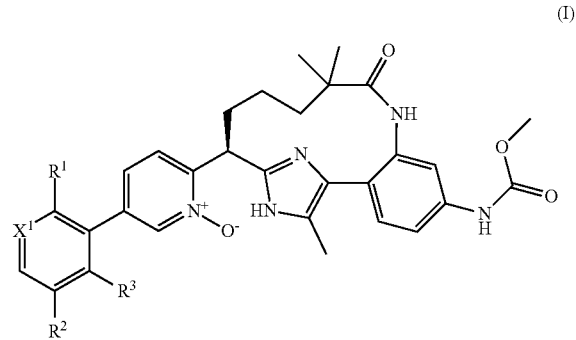

17 Claims, No Drawings

FACTOR XIa INHIBITORS

CROSS REFERENCE TO RELATED APPLICATIONS

This application is a U.S. National Phase application under 35 U.S.C. § 371 of PCT Application No. PCT/US2019/057119 filed Oct. 21, 2019, which claims priority to U.S. Ser. No. 62/750,474 filed Oct. 25, 2018.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel, blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo.

Plasma kallikrein is a zymogen of a trypsin-like serine protease and is present in plasma. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Patients presenting genetic deficiency on C1-esterase inhibitor suffer from hereditary angioedema (HAE), a lifelong disease that results in intermittent swelling throughout the body, including the hands, feet, face, throat, genitals and gastrointestinal tract. Analysis of blisters arising from acute episodes have been shown to contain high levels of plasma kallikrein, and treatment with a protein-based reversible plasma kallikrein inhibitor, Ecallantide (Kalbitor), has been approved by the FDA for the treatment of acute attacks of HAE (Schneider, L, et al., J. Allergy Clin. Immunol., 120: p. 416 (2007)).

Additionally, the plasma kallikrein-kinin system is abnormally abundant in patients diagnosed with advanced diabetic macular edema (DME). Recent publications have shown that plasma kallikrein contributes to observed retinal vascular leakage and dysfunction in diabetic rodent models (A. Clermont, et al., Diabetes, 60:1590 (2011)), and that treatment with a small molecule plasma kallikrein inhibitor ameliorated the observed retinal vascular permeability and other abnormalities related to retinal blood flow.

Factor XIa inhibitor compounds are described in WO2016036893, WO2016015593, WO2016018702, WO2016018701, WO2016011940, JP2015013821, WO2015183709, WO2015120777, WO2015120062, WO2015116885, WO2015116882, WO2015107724, WO2015063093, WO2015047973, WO2015054087, WO2015044174, WO2015044173, WO2015044172, WO2015044170, WO2015044169, WO2015044167, WO2015044165, WO2015044163, WO2015002611, WO2015011087, WO2015123090, WO2015123091, WO2015123093, WO2015164308, WO2014160668, WO2014160592, WO2014059214, WO2014059203, WO2014059202, WO2014022767, WO2014022766, WO2014014050, WO2013174937, WO2013022814, WO2013022818, WO2013055984, WO2013056034, WO2013056060, WO2013118805. WO2013093484.WO2002042273, WO2002037937, WO2002060894, WO2003015715, WO2004002405, US20040180855, WO2004080971, WO2004094372, 0520050228000, US20050282805, WO2005123680, US20090036438, US20120088758, US20060074103, WO2006062972, WO2006076246, US20060154915, US20090062287, US20060183771, WO2007070818, WO2007070816, WO2007070826, WO2008076805, WO2008157162, WO2009114677, WO2011100402, WO2011100401, WO2016118403, WO2016168098, WO2017095760, WO2017074833 and WO2017074832.

SUMMARY OF THE INVENTION

The Present Invention Relates to Compounds of Formula I:

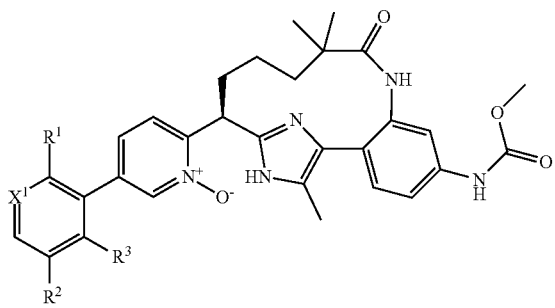

I and pharmaceutically acceptable salts thereof. The compounds of Formula I are selective Factor XIa inhibitors or dual inhibitors of Factor XIa and plasma kallikrein, and as such may be useful in the treatment, inhibition or amelioration of one or more disease states that could benefit from inhibition of Factor XIa or plasma kallikrein, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The Present Invention Relates to Compounds of Formula I:

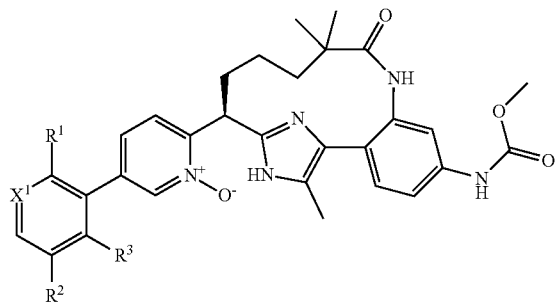

I wherein $R^1$ is $OCHF_2$ when $X^1$ is N; or $R^1$ is a pyrazole optionally substituted with $R^4$ when $X^1$ is CH;

$R^2$ is chloro or fluoro;

$R^3$ is hydrogen or fluoro;

$R^4$ is $CHF_2$ or $CF_3$;

XI is CH or N;

or a pharmaceutically acceptable salt thereof.

Another Embodiment of the Invention Relates to Compounds of Formula Ia:

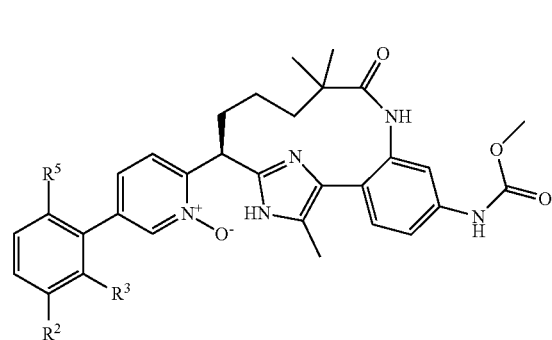

Ia wherein $R^2$ is chloro or fluoro;

$R^3$ is hydrogen or fluoro;

$R^4$ is $CHF_2$ or $CF_3$;

$R^5$ is a pyrazole optionally substituted with $R^4$, or a pharmaceutically acceptable salt thereof Another Embodiment of the Invention Relates to Compounds of Formula Ib:

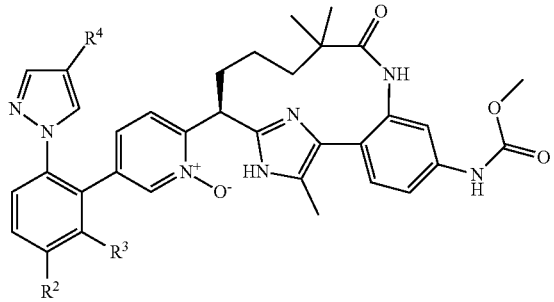

wherein
R² is chloro or fluoro;
R³ is hydrogen or fluoro;
R⁴ is CHF₂ or CF₃;
or a pharmaceutically acceptable salt thereof.
An Embodiment of the Present Invention Relates to Compounds of Formula Ic:

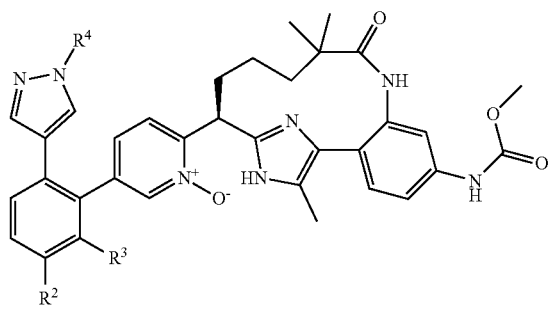

wherein
R² is chloro or fluoro;
R³ is hydrogen or fluoro;
R⁴ is CHF₂ or CF₃;
or a pharmaceutically acceptable salt thereof.
Another Embodiment of the Invention Relates to Compounds of Formula Id:

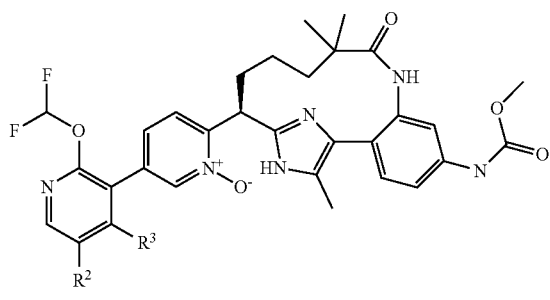

wherein
R² is chloro or fluoro;
R³ is hydrogen or fluoro;
or a pharmaceutically acceptable salt thereof.

In an embodiment of the invention, $R^1$ is $OCHF_2$. In an embodiment of the invention, $R^1$ is a pyrazole optionally substituted with $R^4$. In an embodiment of the invention, $R^1$ is

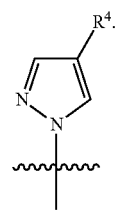

In an embodiment of the invention, $R^1$ is

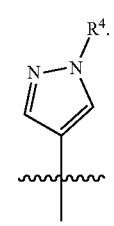

In an embodiment of the invention, $R^2$ is chloro. In an embodiment of the invention, $R^2$ is fluoro.

In an embodiment of the invention, $R^3$ is hydrogen. In an embodiment of the invention, $R^3$ is fluoro.

In an embodiment of the invention, $R^4$ is $CHF_2$. In an embodiment of the invention, $R^4$ is $CF_3$.

In an embodiment of the invention, $X^1$ is CH. In an embodiment of the invention, $X^1$ is N.

In an Embodiment of the Invention, the Compound of Formula I is

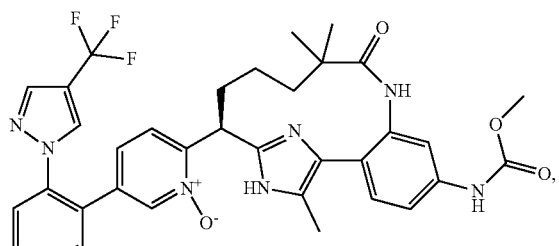

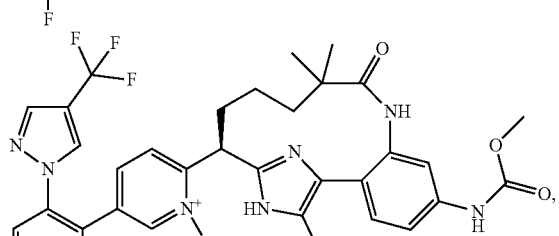

-continued

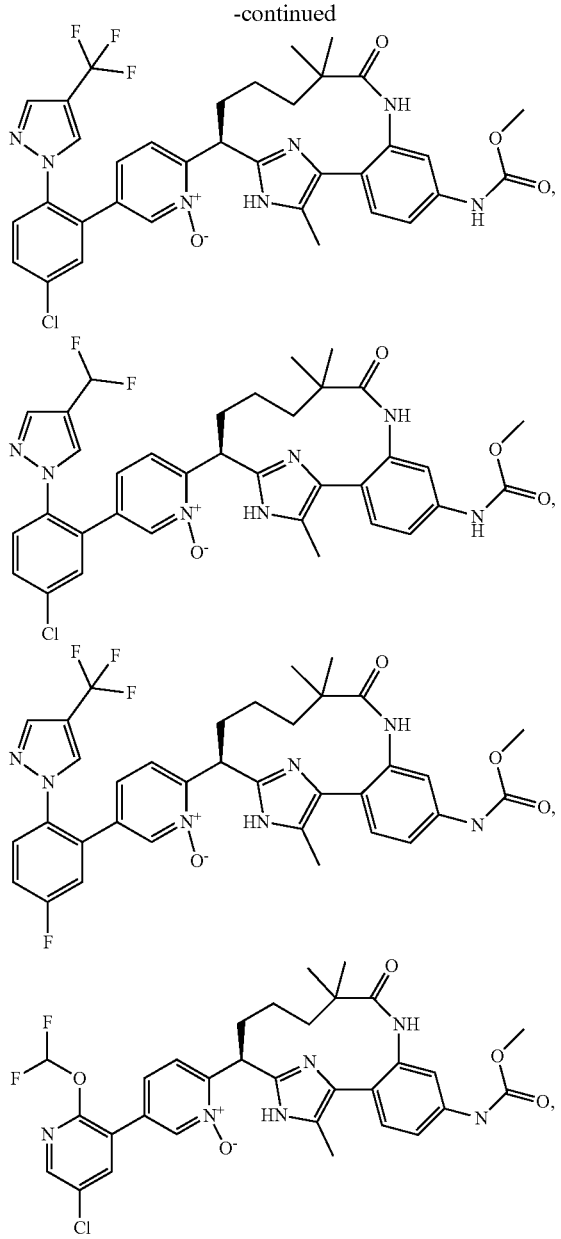

or a pharmaceutically acceptable salt thereof.

Reference to the preferred classes and subclasses set forth above is meant to include all combinations of particular and preferred groups unless stated otherwise.

Specific embodiments of the present invention include, but are not limited to the compounds identified herein as Examples 1 to 6, or pharmaceutically acceptable salts thereof.

Also included within the scope of the present invention is a pharmaceutical composition which is comprised of a compound of Formula I, Formula Ia, Formula Ib, Formula Ic, or Formula Id as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, treating inflammatory disorders, treating diabetic retinopathy and treating hereditary angioedema in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes methods for treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, comprising administering a composition of the compound of the invention to a mammal in need thereof.

The invention also includes a method for reducing the thrombogenicity of a surface in a mammal by attaching to the surface, either covalently or noncovalently, a compound of the invention.

The invention also includes a compound of the invention, or a pharmaceutically acceptable salt thereof, for use in the manufacture of a medicament for inhibiting thrombin, inhibiting thrombus formation, treating thrombus formation or preventing thrombus formation in a mammal. In addition, the invention includes a compound of the invention, or a pharmaceutically acceptable salt thereof, for use in therapy.

Compounds of the invention are Factor XIa inhibitors and may have therapeutic value in, for example, preventing coronary artery disease. The compounds of the invention have improved pharmacokinetic profiles compared to compounds known in the art. Furthermore, some of the compounds of the invention have a better combination of potency, efficacy and pharmacokinetic properties compared to known compounds.

It will be understood that, as used herein, the compounds of the present invention include the pharmaceutically acceptable salts of the compounds of structural Formula I, Formula Ia, Formula Ib, Formula Ic, and Formula Id and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undecenate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, manganous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I, Formula Ia, Formula Ib, Formula Ic or Formula Id simultaneously contain acidic and basic groups in the molecule the invention also includes, in addition to the salt forms mentioned, inner salts or betaines (zwitterions).

The present invention encompasses all stereoisomeric forms of the compounds of Formula I, Formula Ia, Formula Ib, Formula Ic, and Formula Id. Unless a specific stereochemistry is indicated, the present invention is meant to comprehend all such isomeric forms of these compounds. Centers of asymmetry that are present in the compounds of Formula I, Formula Ia, Formula Ib, Formula Ic and Formula Id can all independently of one another have (R) configuration or (S) configuration. When bonds to the chiral carbon are depicted as straight lines in the structural Formulas of the invention, it is understood that both the (R) and (S) configurations of the chiral carbon, and hence both each individual enantiomer and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

Unless a specific enantiomer or diastereomer is indicated, the invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the transform as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, Formula Ia, Formula Ib, Formula Ic or Formula Id or it can be done on a final racemic product. Absolute stereochemistry, may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($1_H$) and deuterium ($2_H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable occurs more than one time in any constituent, its definition on each occurrence is independent at every other occurrence. Also, combinations of substituents and variables are permissible only if such combinations result in stable compounds. Lines drawn, into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I, Formula Ia, Formula Ib, Formula Ic and Formula Id are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$ alkyl esters and —$C_{1-6}$ alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted, the term "halogen" or "halo" means fluorine, chlorine, bromine or iodine.

"Celite®" (Fluka) diatomite is diatomaceous earth, and can be referred to as "celite".

Except where noted herein, bicyclic ring systems include fused ring systems, where two rings share two atoms, and spiro ring systems, where two rings share one atom.

The invention also relates to medicaments containing at least one compound of the Formula I, Formula Ia, Formula Ib, Formula Ic, or Formula Id and/or of a pharmaceutically acceptable salt of the compound of the Formula I, Formula Ia, Formula Ib, Formula Ic or Formula Id and/or an optionally stereoisomeric form of the compound of the Formula I, Formula Ia, Formula Ib, Formula Ic, or Formula Id or a pharmaceutically acceptable salt of the stereoisomeric form of the compound of Formula I, Formula Ia, Formula Ib, Formula Ic or Formula Id, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

The compounds may be selective. Factor XIa inhibitors or dual inhibitors of Factor XIa and plasma kallikrein. Factor XIa or dual Factor XIa/plasma kallikrein inhibition are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor XIa or dual Factor XIa/plasma kallikrein inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples, of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formulas I, Ia, Ib, Ic, and Id and other surfaces which come into contact with blood in the body is possible.

The invention also relates to a process for the production of a medicament, which comprises bringing at least one compound of the Formulas I, Ia, Ib, Ic and Id into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or, sesame oil, polyethylene glycol and solvents such as, for example, sterile water and mono- or polyhydric alcohols such as glycerol.

The dosage regimen utilizing the Factor XIa inhibitors or dual Factor XIa/plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors or dual Factor XIa/plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-5.0 mg/kg/day, and most preferably 1.25-5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-400 mg/day, and most preferably 100-400 mg/day. A suitably prepared medicament for once a day administration would thus contain between 0.8 mg and 2.4 g, preferably between 2 mg and 600 mg, more preferably between 8 mg and 400 mg, and most preferably 100 mg and 400 mg, e.g., 100 mg, 105 mg, 110 mg and 400 mg. Advantageously, the Factor XIa inhibitors may be administered in divided doses of two, three, or four times daily. For administration twice a day, a suitably prepared medicament would contain between 0.4 mg and 1.2 g, preferably between 1 mg and 300 mg, more preferably between 4 mg and 200 mg, and most preferably 50 mg and 200 mg, e.g., 50 mg, 55 mg, 60 mg and 200 mg.

Intravenously, the patient would receive the active ingredient in quantities sufficient to deliver between 0.025-7.5 mg/kg/day, preferably 0.1-5.0 mg/kg/day, and more preferably 1.25-5.0 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I, Formula Ia, Formula Ib, Formula Ic and Formula Id can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors or dual Factor XIa/plasma kallikrein inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g., olmesartan medoxomil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, eplerenone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipin, nimodipine, nicardipine); potassium channel activators (e.g., nicorandil, pinacidil, cromakalim, minoxidil, aprilkalim, loprazolam); sympatholytics; beta-adrenergic blocking drugs (e.g., acebutolol, atenolol, betaxolol, bisoprolol, carvedilol, metoprolol, metoprolol tartrate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin, remogliflozin and sotagliflozin), and SGLT-3; or with other drugs beneficial for the prevention or the treatment of the above-mentioned diseases including but not limited to diazoxide;

and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors or Factor XIa/plasma kallikrein inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

GENERAL METHODS

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are carried out by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. Because the schemes are an illustration, the invention should not be construed as being limited by the chemical reactions and conditions expressed. The preparation of the various starting materials used herein is well within the skill of a person versed in the art. The following examples are provided so that the invention might be more fully understood. These examples are illustrative only and should not be construed as limiting the invention in any way. Absolute stereochemistry of separate stereoisomers in the examples and intermediates are not determined unless stated otherwise in an example or explicitly in the nomenclature.

Abbreviations are Used and Defined as Follows:
S-(+)-DTBM-Segphos® (S)-(+)-5,5'-Bis[di(3,5-di-tert-butyl-4-methoxyphenyl)phosphino]-4,4'-bi-1,3-benzodioxole
X-Phos Pd G2 Chloro(2-dicyclohexylphosphino-2',4',6'-triisopropyl-1,1'-biphenyl)[2-(2'-amino-1,1'-biphenyl)]palladium(II)
cataCXium® A Pd G2 chloro[di(1-adamantyl)-N-butylphosphine)-2-(2-aminobiphenyl)]palladium (II)
Ac acetyl
Ar aryl
aq Aqueous
Bn benzyl
Boc tert-butyloxycarbonyl
t-Bu tert-butyl
DAST diethylaminosulfurtrifluoride
DCE dichloroethane
DCM dichloromethane
DEA diethylamine
DIAD diethyl azodicarboxylate
DIEA or DIPEA N,N-diisopropylethylamine
DME 1,2-dimethoxyethane
DMF Dimethylformamide
DMPU 1,3-dimethyl-Tetrahydropyrimidin-2 (1H)-one
DMSO dimethyl sulfoxide
DPPA diphenylphosphorylazide
EDC or EDCI N-(3-Dimethylaminopropyl)-N'-ethylcarbodiimide ESMS Electrospray mass spectroscopy
Et ethyl
EtOAc ethyl acetate
Et$_3$N Triethylamine
h hour(s)
HATU 1-[bis(dimethylamino)methylene]-1H-1,2,3-triazolo[4,5-b]pyridinium-3-oxidhexafluorophosphate
Hex hexane
HOBt hydroxybenzotriazole hydrate
HPLC high performance liquid chromatography
IPA isopropanol
LCMS Liquid chromatography mass spectrometry
LDA lithium diisopropylamide
LiHMDS lithium bis(trimethylsilyl)amide
m-CPBA m-chloroperoxybenzoic acid
Me methyl
MeCN acetonitrile
MeOH Methanol
mg milligrams
min minute(s)
μL microliters
mL milliliters
mmol millimoles
NMR nuclear magnetic resonance
MS mass spectrometry
MTBE methyl tert-butyl ether
Pd/C Palladium on Carbon
Ph phenyl
Py pyridine
Pd(dppf)Cl$_2$ [1,1'-Bis(diphenylphosphino)ferrocene]dichloropalladium(II)
PPh$_3$ Triphenylphosphine
TBAI tetrabutylammonium iodide
TEA Triethylamine
TFA trifluoroacetic acid
TFAA trifluoroacetic anhydride
THF tetrahydrofuran
TLC thin-layer chromatography
TMEDA tetramethylethylenediamine
TMS tetramethylsilane
rt room temperature
SEM 2-(trimethylsilyl)ethoxy)methyl
SFC Supercritical Fluid Chromatography NMR spectra were measured on VARIAN NMR Systems (400, 500 or 600 MHz) and BRUKER NMR Systems (400, 500 MHz). Chemical shifts are reported in ppm downfield and up field from TMS and referenced to either internal TMS or solvent resonances ($^1$H NMR: δ 7.27 for CDCl$_3$, δ 2.50 for (CD$_3$)(CHD$_2$)SO, and $^{13}$C NMR: δ 77.02 for CDCl$_3$, δ 39.51 for (CD$_3$)$_2$SO. Coupling constants (J) are expressed in hertz (Hz), and spin multiplicities are given as s (singlet), d (doublet), dd (double doublet), t (triplet), m (multiplet), and br (broad). Chiral resolutions were performed on either Waters Thar 80 SFC or Berger M G II, Thar 80 SFC, Waters 80 SFC, Sepiatec 100 SFC, Waters 200 SFC, Thar 350 SFC, Berger MG III preparative SFC systems. LCMS data were recorded on SHIMADAZU LCMS-2020, SHIMADAZU LCMS-2010EV, or Agilent 1100 series LCMS, or Waters Acquity LCMS instruments using C18 columns employing a MeCN gradient in water containing 0.02 to 0.1% TFA. UV detections were at 220 and/or 254 nm and ESI ionization was used for MS detection.

When chiral resolution was achieved by chromatography using chiral columns, the chiral columns used for SFC chiral resolutions are as indicated.

Also, TLC is thin layer chromatography; UV is ultraviolet; W is watts; wt. % is percentage by weight; xg is times gravity; α$_D$ is the specific rotation of polarized light at 589 nm; ° C. is degrees Celsius; % w/v is percentage in weight of the former agent relative to the volume of the latter agent; Hz is hertz; cpm is counts per minute; δ$_H$ is chemical shift; d is doublet; dd is doublet of doublets; MHz is megahertz; MS is mass spectrum, and a mass spectrum obtained by ESMS may be denoted herein by "LCMS"; m/z is mass to charge ratio; n is normal; N is normal; nm is nanometer; nM is nanomolar.

"Human FXIa Ki (nM)" is Human Factor XIa Ki (nM).

Schemes

Scheme 1 illustrates one synthetic sequence for the preparation of the compounds of this invention. Macrocycles of general formula 6 can be prepared as described in Scheme I. Preparation of intermediate macrocyclic core 2 is described in the intermediates section in detail and general methods related to such systems are described in International Patent Publication WO2017/074832. Compounds such as 1 where Y is a suitably reactive halide can be coupled with an appropriate boronic acid 2 or boronic ester using a Suzuki reaction. Subsequent reduction of the olefin of compound 3 to compound 4 can be carried out in either racemic form or through an asymmetric hydrogenation process. In the case of asymmetric hydrogenation enantiomeric enrichment can be obtained through the use of Rh catalyst/S-(+)-DTBM-Segphos® reagent system. Formation of the N-oxide in 5 can be achieved through oxidation of the pyridine of 4 with an oxidant such as urea hydrogen peroxide. Finally, removal of the SEM protecting group of 5 can be carried out through treatment with TFA to afford compounds of general formula 6.

SCHEME 1

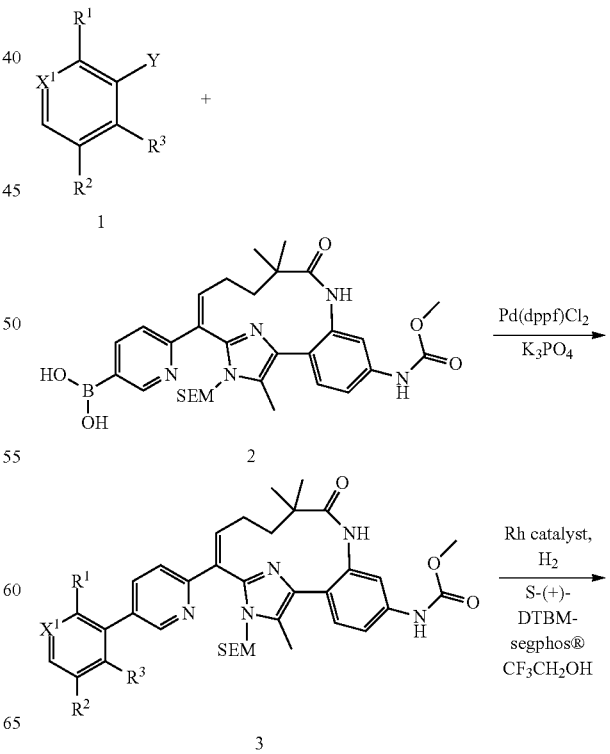

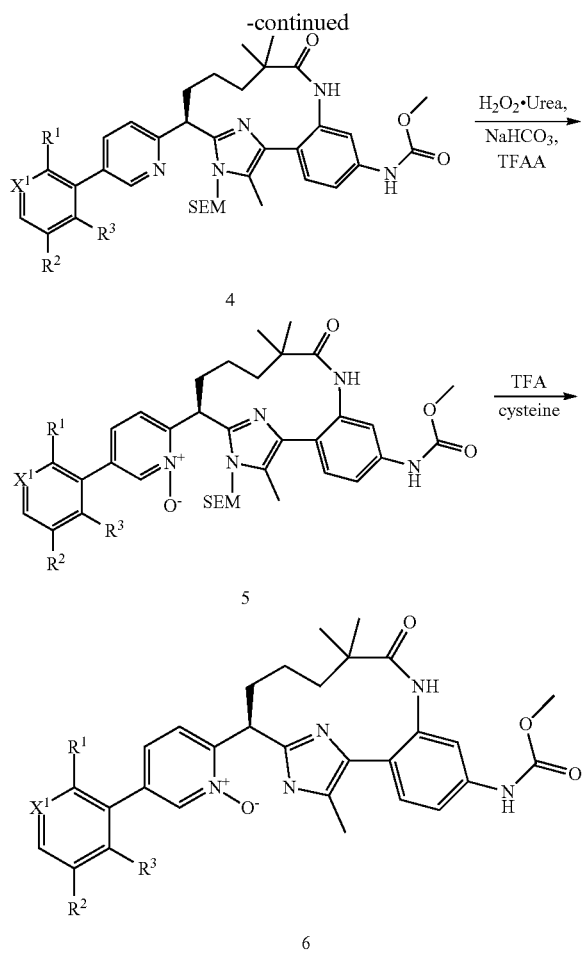

Intermediate 1 methyl (3-amino-4-(4,4,5,5-tetramethyl-1,3,2-dioxaborolan-2-yl)phenyl)carbamate

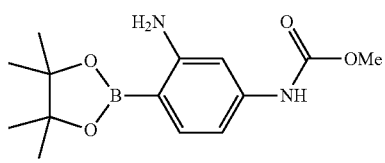 [SMILES: COC(=O)Nc1ccc(B2OC(C)(C)C(C)(C)O2)c(N)c1]

Step 1: (4-bromo-3-nitrophenyl)carbamate

To 4-bromo-3-nitroaniline (500.0 g, 2.30 mol, 1 eq) in 2-Me-THF (2.5 L) was added DIEA (655.0 g, 5.07 mol, 883.0 mL, 2.2 eq) in one portion. Then methyl carbonochloridate (261.0 g, 2.76 mol, 214.0 mL, 1.2 eq) was added to the reaction over 0.5 h while maintaining the temperature between 20-48° C. The reaction was heated to 50° C. and aged for 1 h. It was then cooled to 20° C. The reaction was poured into water and extracted with EtOAc. The combined organic portion was washed with brine, and dried over anhydrous sodium sulfate. The mixture was filtered and, then concentrated under vacuum. The product was slurried with petroleum ether. The product was then collected by filtration and dried under vacuum to afford methyl (4-bromo-3-nitrophenyl)carbamate. $^1$HNMR: (400 MHz, CDCl$_3$) 8.03 (s, 1H), 7.64 (d, J=8.8 Hz, 1H), 7.45-7.47 (m, 1H), 6.99 (s, 1H), 3.81 (s, 3H).

Step 2: methyl (3-nitro-4-(4,4,5,5-tetramethyl-1,3,2-dioxaborolan-2-yl)phenyl)carbamate To a 3 L three necked flask equipped with magnetic stirrer was added methyl (4-bromo-3-nitrophenyl)carbamate (450.0 g, 1.64 mol, 1.0 eq) in dioxane (2.7 L), 4,4,4',4',5,5,5',5'-octamethyl-2,2'-bi(1,3,2-dioxaborolane (456.9 g, 1.80 mol, 1.1 eq), KOAc (353.2 g, 3.60 mol, 2.2 eq) and Pd(dppf)Cl$_2$ (59.8 g, 0.08 mol, 0.05 eq) 25° C. The reaction was purged with N$_2$ three times and then heated to 80° C. and aged for 7 h. The reaction was concentrated under vacuum. The residue was suspended in MTBE. The mixture was filtered, and the filtrate was concentrated under vacuum. The residue was purified by column chromatography (SiO$_2$, Petroleum ether:Ethyl acetate=50:1 to 4:1). The fractions containing the desired product were combined and concentrated under vacuum to afford methyl (3-nitro-4-(4,4,5,5-tetramethyl-1,3,2-dioxaborolan-2-yl)phenyl)carbamate. $^1$HNMR: 400 MHz CDCl$_3$ δ: 8.18 (s, 1H), 7.69-7.71 (d, J=7.2 Hz, 1H), 7.46-7.48 (d, J=8.0 Hz, 1H), 6.96 (s, 1H), 3.80 (s, 3H), 1.42 (s, 12H)

Step 3: methyl (3-amino-4-(4,4,5,5-tetramethyl-1,3,2-dioxaborolan-2-yl)phenyl)carbamate To a dried hydrogenation bottle was added Pd/C (3.0 g, 10.0% purity), MeOH (1.5 L), and methyl (3-nitro-4-(4,4,5,5-tetramethyl-1,3,2-dioxaborolan-2-yl)phenyl)carbamate (60.0 g, 0.18 mol, 1.0 eq). The vessel was degassed under vacuum and purged with H$_2$ three times. The reaction was then aged for 2 h under H$_2$ (20 Psi) at 25° C. The reaction mixture was filtered on celite and the filtrate concentrated under vacuum to afford methyl (3-amino-4-(4,4,5,5-tetramethyl-1,3,2-dioxaborolan-2-yl)phenyl)carbamate. LCMS (ES, m/z): 292.9 [M+H]$^+$.
$^1$HNMR: (400 MHz, CDCl$_3$) 7.51 (d, J=8.0 Hz, 1H), 6.91 (s, 1H), 6.55 (s, 1H), 6.46-6.49 (m, 1H), 4.80 (s, 2H), 3.76 (s, 3H), 1.33 (s, 12H)

Intermediate 2

5-chloro-N-methoxy-N-methylpicolinamide

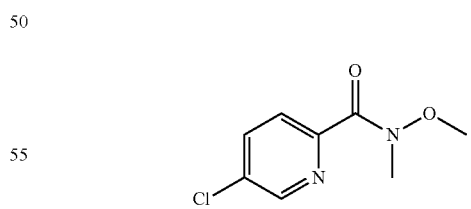

5-Chloropicolinic acid (300.0 g, 1.90 mol, 1.0 eq) and N-methoxymethanamine (278.6 g, 2.86 mol, 1.5 eq, HCl) were added to CH$_2$Cl$_2$ (2.4 L). HOBt (25.7 g, 0.19 mol, 0.1 eq) and EDCI (438.0 g, 2.28 mol, 1.2 eq) were added to the reaction at 15° C. The reaction temperature rose to 20° C. TEA (578.0 g, 5.71 mol, 795.0 mL, 3.0 eq) was added over 0.5 h at 15° C. The inner reaction temperature did not exceed 20° C. The reaction aged 1 h at 15° C. The reactions were poured into ice water (4.0 L) and extracted with CH$_2$Cl$_2$ (1.5

L). The organic layer was washed with water (3.0 L×2) and then dried over anhydrous Na$_2$SO$_4$. It was then filtered, and the filtrate was concentrated under vacuum. The residue was stirred in petroleum ether (3.0 L) for 0.5 h. The material was isolated by filtration and dried under vacuum to afford 5-chloro-N-methoxy-N-methylpicolinamide. $^1$HNMR: 400 MHz CDCl$_3$ δ: 8.57 (s, 1H), 7.75-7.78 (m, 1H), 7.65 (br, 1H), 3.75 (s, 3H), 3.40 (s, 3H)

Intermediate 3 methyl (3-amino-4-(2-(5-chloropicolinoyl)-5-methyl-1-((2-(trimethylsilyl)ethoxy)methyl)-1H-imidazol-4-yl)phenyl)carbamate

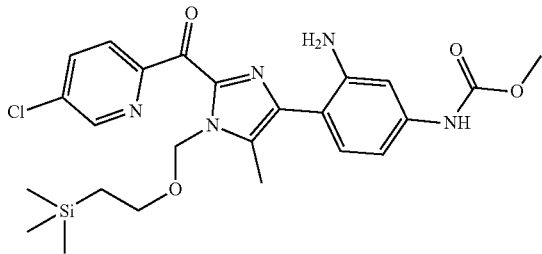 [SMILES: COC(=O)Nc1ccc(-c2nc(C(=O)c3ccc(Cl)cn3)n(COCC[Si](C)(C)C)c2C)c(N)c1]

Step 1: 1-(4-methyl-1H-imidazol-1-yl)ethan-1-one 4-methyl-1H-imidazole (250.0 g, 3.04 mol, 1.0 eq) was combined with MeCN (1.2 L). The reaction was degassed under vacuum and purged with nitrogen three times before cooling to 0° C. with an ice bath. TEA (369.1 g, 3.65 mol, 507.7 mL, 1.2 eq) was added over 0.5 h. Acetyl chloride (257.7 g, 3.28 mol, 234.3 mL, 1.08 eq) was added over 0.5 h. The reaction was warmed to 20° C. and aged for 1 h. The reaction was filtered, and the filter cake washed with MeCN three times. The reaction was concentrated under vacuum to afford 1-(4-methyl-1H-imidazol-1-yl)ethan-1-one which was used in the next step without further purification.

Step 2: 5-methyl-1-((2-(trimethylsilyl)ethoxy)methyl)-1H-imidazole 1-(4-methyl-1H-imidazol-1-yl)ethan-1-one (300.0 g, 2.42 mol, 1.0 eq) was added to MeCN (2.0 L). The reaction vessel was degassed under vacuum and purged with nitrogen three times before cooling to 0° C. with an ice-bath. 2-(Trimethylsilyl)ethoxymethyl chloride (443.2 g, 2.66 mol, 470.5 mL, 1.1 eq) was added at 0° C. over 0.5 h. The reaction was aged at 0° C. for 0.5 h. The reaction was poured into ice water, and the pH of the solution was adjusted to 11 with aqueous NaOH (2.5 M). The solution was extracted with MTBE, and the combined organic phase was washed with brine before drying over anhydrous Na$_2$SO$_4$. The solution was filtered prior to concentration under vacuum to afford 5-methyl-1-((2-(trimethylsilyl)ethoxy)methyl)-1H-imidazole. $^1$HNMR: 400 MHz CDCl$_3$ δ: 7.49 (s, 1H), 6.80 (s, 1H), 5.21 (s, 1H), 3.48 (t, J=16.4 Hz, 2H), 2.27 (s, 3H), 0.92 (t, J=12.4 Hz, 2H), 0.00 (s, 9H).

Step 3: 4-iodo-5-methyl-14(2-(trimethylsilyl)ethoxy)methyl)-1H-imidazole 5-methyl-14(2-(trimethylsilyl)ethoxy)methyl)-1H-imidazole (500.0 g, 2.35 mol, 1.0 eq) was combined with MeCN (2.5 L). To this was added N-Iodosuccinimide (582.6 g, 2.59 mol, 1.1 eq) along with TFA (80.5 g, 0.71 mol, 52.3 mL, 0.3 eq). The reaction was warmed to 70° C. and aged for 1 h. The reaction was cooled to room temperature and combined with saturated aqueous sodium thiosulfate aqueous. The mixture was extracted with EtOAc, and the organic phase was washed with brine and dried over anhydrous Na$_2$SO$_4$. The mixture was filtered, and the solution was concentrated under vacuum. The residue was purified by silica gel chromatography eluted with (Petroleum ether:EtOAc=10:1~1:1) to afford 4-iodo-5-methyl-14(2-(trimethylsilyl)ethoxy)methyl)-1H-imidazole. $^1$HNMR: ET19627-10-P1A 400 MHz CDCl$_3$ δ: 7.51 (s, 1H), 5.21 (m, 2H), 3.46 (t, J=8.0 Hz, 2H), 2.25 (s, 3H), 0.89 (t, J=16.4 Hz, 2H), 0.02 (s, 9H).

Step 4: (5-chloropyridin-2-yl)(4-iodo-5-methyl-1-((2-(trimethylsilyl)ethoxy)methyl)-1H-imidazol-2-yl)methanone To THF (1.5 L) was added 4-iodo-5-methyl-1((2-(trimethylsilyl)ethoxy)methyl)-1H-imidazole (320.0 g, 0.94 mol, 1.0 eq), and the reaction vessel was purged with N$_2$ three times. The reaction was cooled to −65° C. LDA (2 M in THF, 520.0 mL, 1.1 eq) was added dropwise at −65° C. and the reaction aged at −65° C. for 1 h. 5-chloro-N-methoxy-N-methylpicolinamide (189.8 g, 0.94 mol, 1.0 eq) in THF (0.5 L) was added dropwise to the solution at −65° C., and the reaction aged at −65° C. for 1 h. The reaction was then added to saturated aqueous NH$_4$Cl at 0° C. and extracted with EtOAc (2×). The combined organic portion was washed with brine and then dried over Na$_2$SO$_4$, filtered, and concentrated under vacuum. The residue was purified by column chromatography (SiO$_2$, Petroleum ether:Ethyl acetate=1:0 to 3:1). The fractions containing the desired product were combined and concentrated under vacuum to afford (5-chloropyridin-2-yl)(4-iodo-5-methyl-1-((2-(trimethylsilyl)ethoxy)methyl)-1H-imidazol-2-yl)methanone. $^1$HNMR: 400 MHz, CDCl$_3$ δ: 8.76 (s, 1H), 8.21-8.23 (d, J=8.4 Hz, 1H), 7.86-7.88 (m, 1H), 5.91 (s, 2H), 3.68 (t, J=8.2 Hz, 2H), 2.44 (s, 3H), J=8.2 Hz, 2H), 0.00 (s, 9H).

Step 5: methyl (3-amino-4-(2-(5-chloropicolinoyl)-5-methyl-1-((2-(trimethylsilyl)ethoxy)methyl)-1H-imidazol-4-yl)phenyl)carbamate To (5-chloropyridin-2-yl)(4-iodo-5-methyl-1-((2-(trimethylsilyl)ethoxy)methyl)-1H-imidazol-2-yl)methanone (200.0 g, 0.42 mol, 1.0 eq) was added dioxane (1.5 L), H$_2$O (0.5 L), methyl (3-amino-4-(4,4,5,5-tetramethyl-1,3,2-dioxaborolan-2-yl)phenyl)carbamate (134.5 g, 0.46 mol, 1.1 eq), Pd(PPh$_3$)$_4$ (48.4 g, 0.042 mol, 0.1 eq) and K$_3$PO$_4$ (266.6 g, 1.26 mol, 3 eq). The reaction was purged with N$_2$ three times. The reaction was heated to 80° C. and aged for 12 h. The reaction was cooled to 25° C. before dilution with water. It was extracted with EtOAc (2×), and the combined organic portion was concentrated under vacuum. The residue was purified by column chromatography (SiO$_2$, Petroleum ether: Ethyl acetate=10:1 to 1:1). The fractions containing the desired product were combined and concentrated under vacuum. The residue was further purified by prep-HPLC (column: Phenomenex luna(2) C18 20~35 um; mobile phase: [water (0.1% TFA)-MeOH]; B %: 50%-75%, 40 min, 75%-75%, 60 min). The fractions containing the desired product were combined and concentrated under vacuum to afford methyl (3-amino-4-(2-(5-chloropicolinoyl)-5-methyl-1-((2-(trimethylsilyl)ethoxy)methyl)-1H-imidazol-4-yl)phenyl)carbamate. $^1$HNMR: (400 MHz, CDCl$_3$) δ: 8.72 (s, 1H), 8.16-8.18 (d, J=8.4, 1H), 7.81-7.83 (m, 1H), 7.15-7.17 (d, J=8.4, 1H), 6.98 (s, 1H), 6.68-6.70 (m, 1H), 6.54 (s, 1H), 5.95 (s, 2H), 4.97 (s, 2H), 3.79 (s, 3H), 3.73 (t, J=8.4, 2H), 2.52 (s, 3H), 0.97 (t, J=8.4, 2H), 0.00(s, 9H). LCMS (ES, m/z): 516.2 [M+H]$^+$.

Intermediate 4

5-(benzo[d]thiazol-2-ylsulfonyl)-2,2-dimethylpentanoic Acid

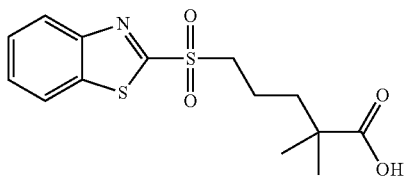 [SMILES: CC(C)(CCCS(=O)(=O)c1nc2ccccc2s1)C(=O)O]

Step 1: methyl 5-(benzo[d]thiazol-2-ylthio)pentanoate

Benzo[d]thiazole-2-thiol (220 g, 1.32 mol) and methyl 5-bromopentanoate (282.2 g, 1.45 mol) were combined with acetone (2.0 L) in a three-necked round bottom flask equipped with magnetic stirrer at 20° C. To this was added K$_2$CO$_3$ (181.8 g, 1.32 mol) in one portion at 20° C. The reaction was stirred at 20° C. for 12 hours. The reaction was filtered, and concentrated under vacuum to provide methyl 5-(benzo[d]thiazol-2-ylthio)pentanoate that was used for the next step without further purification.

Step 2: methyl 5-(benzo[d]thiazol-2-ylthio)-2-methylpentanoate

A three-necked round bottom flask equipped with magnetic stirrer was charged with methyl 5-(benzo[d]thiazol-2-ylthio)pentanoate (300.0 g, 1.07 mol) and CH$_3$I (151.3 g, 1.07 mol) in dry THF (1.5 L) at 20° C. The reaction was cooled to −70° C. before addition of LiHMDS (2 M in THF, 746.3 ml) to the mixture over 2 hours while maintaining the temperature below −60° C. The reaction aged at −60° C. for 2 hours. The reaction mixture was poured into saturated aqueous NH$_4$Cl (8.0 L) and extracted with ethyl acetate. The organic phase was washed with brine and then concentrated under vacuum. The residue was purified by silica gel chromatography. The fractions containing the desired product were combined and concentrated under vacuum to afford methyl 5-(benzo[d]thiazol-2-ylthio)pentanoate.

Step 3: methyl 5-(benzo[d]thiazol-2-ylthio)-2,2-dimethylpentanoate

A three-necked round bottom flask equipped with magnetic stirrer was charged with methyl 5-(benzo[d]thiazol-2-ylthio)-2-methylpentanoate (200.0 g, 0.68 mol) and CH$_3$I (283.5 g, 2.0 mol) in dry THF (1.0 L) at 20° C. The reaction was cooled to −70° C. before addition of LDA (2 M, 0.88 L) to the mixture over 2 hours while maintaining the temperature below −60° C. The reaction aged at −60° C. for 2 hours. The reaction mixture was poured into saturated aqueous NH$_4$Cl (4.0 L) and extracted with ethyl acetate twice (5.0 L, 4.0 L). The organic phase was washed with brine (5.0 L) and then concentrated under vacuum to afford methyl 5-(benzo [d]thiazol-2-ylthio)-2,2-dimethylpentanoate which was used for the next step without further purification.

Step 4: 5-(benzo[d]thiazol-2-ylthio)-2,2-dimethylpentanoic Acid

A three-necked round bottom flask equipped with magnetic stirrer was charged with methyl 5-(benzo[d]thiazol-2-ylthio)-2,2-dimethylpentanoate (200.0 g, 0.64 mol) in 2-methyltetrahydrofuran (0.2 L) at 20° C. Aq. NaOH (3.75 M, 1.0 L) was added in one portion to the mixture at 20° C. The mixture aged at 80° C. reflux for 15 hours. After cooling to room temperate the reaction was extracted with ethyl acetate, and the aqueous phase was adjusted to pH=2 with aq. HCl (4 M, 1.0 L) to allow precipitation of solid. The solid was filtered, and the filter cake was washed with petroleum ether to afford 5-(benzo[d]thiazol-2-ylthio)-2,2-dimethylpentanoic acid that was used for the next step without further purification.

Step 5: 5-(benzo[d]thiazol-2-ylsulfonyl)-2,2-dimethylpentanoic Acid

A three-necked round bottom flask, equipped with magnetic stirrer was charged with 5-(benzo[d]thiazol-2-ylthio)-2,2-dimethylpentanoic acid (730.0 g, 2.48 mol) in EtOH (3600 ml) at 20° C. To this was added ammonium molybdate (73 g) in one portion at 20° C. H$_2$O$_2$ (1403 g, 12.4 mol, 30% purity) was added to the mixture at 20° C. over 0.2 hr. The reaction aged at ~20-30° C. for 2 hours at which point water (15 L) was added at 20° C. The mixture was extracted with ethyl acetate. The organic phase washed with saturated aqueous Na$_2$SO$_3$ (4.0 L×3), and then dried over Na$_2$SO$_4$. The mixture was filtered, and the filtrate was concentrated under vacuum. The product was triturated with petroleum ether:ethyl acetate=1:1 to afford 5-(benzo[d]thiazol-2-ylsulfonyl)-2,2-dimethylpentanoic acid. LCMS (ES, m/z): 328.0 [M+H]$^+$.

Intermediate 5 methyl (1$^2$Z,8Z)-9-(5-chloropyridin-2-yl)-1$^5$,5,5-trimethyl-4-oxo-1$^1$-((2-(trimethylsilyl)ethoxy)methyl)-1$^1$H-3-aza-1(4,2)- imidazola-2(1,2)-benzenacyclononaphan-8-en-2$^4$-yl)carbamate

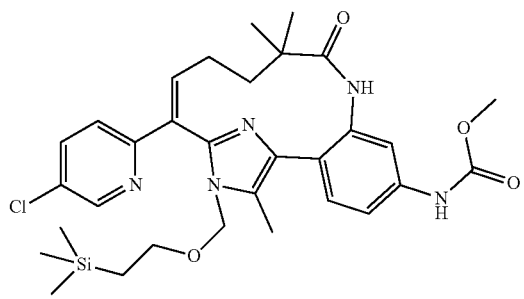 [SMILES: COC(=O)Nc1ccc2c(c1)NC(=O)C(C)(C)CC/C=C(/c1ccc(Cl)cn1)c1nc-2c(C)n1COCC[Si](C)(C)C]

Step 1: 5-(benzo[d]thiazol-2-ylsulfonyl)-2,2-dimethylpentanoyl Chloride

A mixture of 5-(benzo[d]thiazol-2-ylsulfonyl)-2,2-dimethylpentanoic acid (75 g, 229.1 mmol) and sulfurous dichloride (450 mL) in toluene (1500 mL) was heated at 110° C. for 16 h. The mixture was concentrated under vacuum to afford 5-(benzo[d]thiazol-2-ylsulfonyl)-2,2-dimethylpentanoyl chloride which was used in the next step without further purification.

Step 2: methyl (3-(5-(benzo[d]thiazol-2-ylsulfonyl)-2,2-dimethylpentanamido)-4-(2-(5-chloropicolinoyl)-5-methyl-1-((2-(trimethylsilyl)ethoxy)methyl)-1H-imidazol-4-yl)phenylcarbamate A mixture of 5-(benzo[d]thiazol-2-ylsulfonyl)-2,2-dimethylpentanoyl chloride (80 g), Et$_3$N (46.3 g, 458.2 mmol) and methyl(3-amino-4-(2-(5-chloropicolinoyl)-5-methyl-1-((2-(trimethylsilyl)ethoxy)methyl)-1H-imidazol-4-yl)phenyl)carbamate (112.3 g, 217.6 mmol) in DCM (1500 mL) was stirred at 15° C. for 16 h. NH$_3$H$_2$O (80 mL) was added, and the reaction aged for 30 min. The resulting mixture was washed with 1500 mL of H$_2$O and 2×1500 mL of 0.5N HCl. The organic portion was washed with 1500 mL of brine and concentrated under vacuum to afford the title compound that was used in the next step without additional purification. LCMS (ES, m/z): 825 [M+H]$^+$.

Step 3: methyl (1$^2$Z,8Z)-9-(5-chloropyridin-2-yl)-1$^5$,5,5-trimethyl-4-oxo-1$^1$-((2-(trimethylsilyl)methyl)-1$^1$H-3-aza-1(4,2)-imidazola-2(1,2)-benzenacyclononaphan-8-en-2$^4$-yl)carbamate To a solution of methyl (3-(5-(benzo[d]thiazol-2-ylsulfonyl)-2,2-dimethylpentanamido)-4-(2-(5-chloropicolinoyl)-5-methyl-1-(2-(trimethylsilyl)ethoxy)methyl)-1H-imidazol-4-yl)phenyl)carbamate (184 g) in THF (1840 mL) was added LiHMDS (1832 mL, 1832 mmol, 1 M in THF) at −78° C. under N$_2$ atmosphere. The reaction mixture was aged at the same temperature for 4 h at which point the reaction was quenched with saturated NH$_4$Cl (2000 mL) and washed with 5% NaOH (2000 mL×3) and saturated aqueous NaCl (2000 mL). The combined organic layers was dried with Na$_2$SO$_4$, filtered, and concentrated under vacuum. The product was slurried with petroleum ether/EtOAc (1500 mL/30 mL), filtered, and dried to afford the title compound. LCMS (ES, m/z): 610 [M+H]$^+$.

Intermediate 6

(6-((1$^2$Z,8Z)-2$^4$-((methoxycarbonyl)amino)-1$^5$,5,5-trimethyl-4-oxo-1$^1$-((2-(trimethylsilyl)ethoxy)methyl)-1$^1$H-3-aza-1(4,2)-imidazola-2(1,2)-benzenacyclononaphan-8-en-9-yl)pyridin-3-yl)boronic Acid

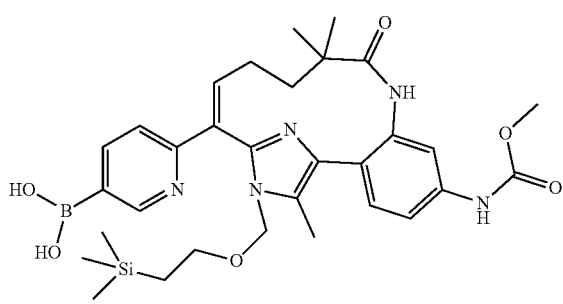 [SMILES: COC(=O)Nc1ccc2c(c1)NC(=O)C(C)(C)CC/C=C(/c1ccc(B(O)O)cn1)c1nc-2c(C)n1COCC[Si](C)(C)C]

To a stirred mixture of methyl ((1$^2$Z,8Z)-9-(5-chloropyridin-2-yl)-1$^5$,5,5-trimethyl-4-oxo-1$^1$-((2-(trimethylsilyl)ethoxy)methyl)-1$^1$H-3-aza-1(4,2)-imidazola-2(1,2)-benzenacyclononaphan-8-en-2$^4$-yl)carbamate (21 g, 34.4 mmol), potassium acetate (10.13 g, 103 mmol), 4,4,4',4',5,5,5',5'-octamethyl-2,2'-bi(1,3,2-dioxaborolane) (11.36 g, 44.7 mmol) in dioxane (300 mL) was added X-Phos Pd G2, chloro(2-dicyclohexylphosphino-2',4',6'-triisopropyl-1,1'-biphenyl)[2-(2'-amino-1,1'-biphenyl)]palladium(II) (1.895 g, 2.409 mmol) under N$_2$ at 25° C., and the mixture was stirred at 90° C. for 1.5 h under N$_2$. LCMS showed the reaction was completed. Water (200 mL) was added, and the mixture was extracted with ethyl acetate (2×200 mL). The combined organic fractions were washed with brine (200 mL), dried over Na$_2$SO$_4$, filtered, and the solvent was evaporated under reduced pressure. The residue was used in next step without further purification. LCMS (ES, m/z): 620.5 [M+H]$^+$.

Example 1

(R,Z)-5-(2,3-difluoro-6-(4-(trifluoromethyl)-1H-pyrazol-1-yl)phenyl)-2-(2$^4$-((methoxycarbonyl)amino)-1$^5$,5,5-trimethyl-4-oxo-1$^1$H-3-aza-1(4,2)-imidazola-2 (1,2)-benzenacyclononaphane-9-yl) pyridine 1-oxide

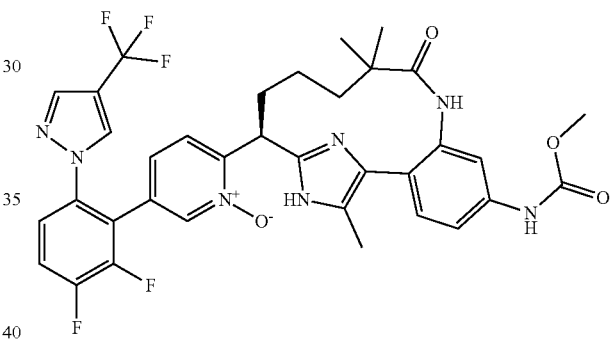

Step 1: (Z)—N-(3-(dimethylamino)-2-(trifluoromethyl)allylidene)-N-methylmethanaminium Hexafluorophosphate (V)

To a stirred mixture of phosphoryl trichloride (5.82 mL, 62.5 mmol) in DMF (15 mL) was added 3,3,3-trifluoropropanoic acid (4 g, 31.2 mmol) at ambient temperature. The reaction mixture was stirred at 50° C. for 4 h under N$_2$ atmosphere. It was then cooled to ambient temperature and slowly added to a solution of sodium hexafluorophosphate (V) (2.214 mL, 31.2 mmol) in water (50 mL) at 0° C. over 30 minutes, while maintaining the internal temperature below 10° C. Sodium hydroxide (10 M) was added until the pH was 4. The mixture was stirred for 1 h and filtered. The filter cake was washed with water (50 mL) and dried under vacuum to give the title compound.

Step 2: (2-bromo-3,4-difluorophenyl)hydrazine

To a stirred mixture of 2-bromo-3,4-difluoroaniline (2 g, 9.62 mmol) in hydrogen chloride (12N, 20 mL) was added sodium nitrite (0.663 g, 9.62 mmol) in water (2 mL) at 0° C., and the mixture was stirred at 0° C. for 30 min. Tin(II) chloride dihydrate (6.51 g, 28.8 mmol) in 12N hydrogen chloride (20 mL) was added at 0° C. The mixture was stirred at 25° C. for 16 h. The mixture was filtered, and the filter cake was washed with water (50 mL), and subsequently concentrated to dryness to give the title compound.

Step 3: 1-(2-bromo-3,4-difluorophenyl)-4-(trifluoromethyl)-1H-pyrazole

To a stirred mixture of (2-bromo-3,4-difluorophenyl)hydrazine (1 g, 4.48 mmol), (2)—N-(3-(dimethylamino)-2-(trifluoromethyl)allylidene)-N-methylmethanaminium hexafluorophosphate (V) (1.525 g, 4.48 mmol) in THF (20 mL) at 25° C. was added sodium methoxide (0.291 g, 5.38 mmol). The reaction mixture was stirred at 25° C. for 16 h under $N_2$ atmosphere. Trifluoroacetic acid (3 mL, 38.9 mmol) was added, and the mixture was stirred at 80° C. for 5 h. LCMS showed the reaction was completed. The mixture was concentrated. The residue was purified by column chromatography on silica (0-5% EtOAc/petroleum ether) to give the title compound.

Step 4: methyl (($1^2Z,8Z$)-9-(5-(2,3-difluoro-6-(4-(trifluoromethyl)-1H-pyrazol-1-yl)phenyl)pyridin-2-yl)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphan-8-en-$2^4$-yl)carbamate To a stirred mixture of (6-(($1^2Z,8Z$)-$2^4$-((methoxycarbonyl)amino)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphan-8-en-9-yl)(pyridin-3-yl)boronic acid (1.3 g, 1.6798 mmol), 1-(2-bromo-3,4-difluorophenyl)-4-(trifluoromethyl)-1H-pyrazole (0.604 g, 1.846 mmol), potassium phosphate (2 M in water, 2.52 mL, 5.04 mmol) in dioxane (30 mL) at 25° C. was added [1,1'-bis(diphenylphosphino)ferrocene]dichloropalladium(II) (0.098 g, 0.134 mmol) under $N_2$, and the mixture was stirred at 80° C. under $N_2$ for 16 h. LCMS showed that the reaction completed. The mixture was cooled, diluted with ethyl acetate (100 mL), washed with brine (50 mL), dried over $Na_2SO_4$, filtered, and the solvent was evaporated under reduced pressure. The residue was purified by column chromatography on silica (0-35% EtOAc/petroleum ether) to give the title compound. LCMS (ES, m/z): 822.6 $[M+H]^+$.

Step 5: methyl (R.Z)-(9-(5-(2,3-difluoro-6-(4-(trifluoromethyl)-1H-pyrazol-1-yl)phenylpyridin-2-yl)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphane-$2^4$-yl)carbamate To a stirred mixture of bis(norbornadiene)rhodium(I) tetrafluoroborate (0.050 g, 0.134 mmol) in 1,2-dichloroethane (2 mL) was added (S)-(+)-5,5'-bis[di(3,5-di-tert-butyl-4-methoxyphenyl)phosphino]-4,4'-bi-1,3-benzodioxole (0.166 g, 0.141 mmol) at 25° C. in glove box, and the mixture was stirred at 25° C. for 1 h. The mixture of methyl (($1^2Z,8Z$)-9-(5-(2,3-difluoro-6-(4-(trifluoromethyl)-1H-pyrazol-1-yl)phenyl)pyridin-2-yl)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphan-8-en-$2^4$-yl)carbamate (1.1 g, 1.338 mmol) in 2,2,2-trifluoroethan-1-ol (10 mL) was added to the above mixture, and the resulting reaction mixture was stirred at 50° C. for 16 h under $H_2$ at 50 Psi. LCMS showed the reaction was completed. The mixture was concentrated to give the title compound. LCMS (ES, m/z): 824.5 $[M+H]^+$.

Step 6: (R.Z)-5-(2,3-difluoro-6-(4-(trifluoromethyl)-1H-pyrazol-1-yl)phenyl)-2-($2^4$-((methoxycarbonyl)amino)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphane-9-yl)pyridine 1-oxide To a stirred mixture of urea hydrogen peroxide (0.457 g, 4.85 mmol), sodium bicarbonate (0.816 g, 9.71 mmol) in dichloromethane (15 mL) at 0° C. was added trifluoroacetic anhydride (0.686 mL, 4.85 mmol), and the mixture was stirred at 0° C. for 10 min. Then a solution of methyl (R.Z)-(9-(5-(2,3-difluoro-6-(4-(trifluoromethyl)-1H-pyrazol-1-yl)phenyl)pyridin-2-yl)-$1^5$, 5,5-trimethyl-4-oxo-$1^1$-((2-(trimethylsilyl)ethoxy)methyl)-$1^1$H-3-aza-1(4,2)-imidazola-2(1,2)-benzenacyclononaphane-$2^4$-yl)carbamate (1 g, 1.214 mmol) in dichloromethane (50 mL) was added, and the mixture was stirred for 1 h. LCMS showed the reaction was completed. Water (100 mL) was added, and the mixture was extracted with dichloromethane (2×200 mL). The combined organic fractions were washed with aqueous $Na_2SO_3$ (20%, 200 mL) and brine (200 mL), dried over $Na_2SO_4$, filtered, and the solvent was evaporated under reduced pressure to afford the title compound which was used in the next step without further purification. LCMS (ES, m/z): 840.5 $[M+H]^+$.

Step 7: (R.Z)-5-(2,3-difluoro-6-(4-(trifluoromethyl)-1H-pyrazol-1-yl)phenyl)-2-($2^4$-((methoxycarbonyl)amino)-$1^5$,5,5-trimethyl-4-oxo-$1^1$H-3-aza-1(4,2)-imidazola-2(1,2)-benzenacyclononaphane-9-yl) pyridine 1-oxide To a stirred mixture of (R.Z)-5-(2,3-difluoro-6-(4-(trifluoromethyl)-1H-pyrazol-1-yl)phenyl)-2-($2^4$-((methoxycarbonyl)amino)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphane-9-yl)pyridine 1-oxide (1 g, 1.191 mmol), (R)-2-amino-3-mercaptopropanoic acid (0.577 g, 4.76 mmol) in dichloromethane (5 mL) was added 2,2,2-trifluoroacetic acid (10 mL, 1.191 mmol) at ambient temperature, and the reaction mixture was stirred at 40° C. for 4 h. LCMS showed the reaction was completed. The mixture was concentrated. The residue was diluted with ethyl acetate (50 mL), washed with aqueous sodium hydrogen carbonate (50 mL). The aqueous layer was extracted with ethyl acetate (2×30 mL). The combined organic layers were dried over $Na_2SO_4$, filtered, and the solvent was evaporated under reduced pressure. The residue was purified by column chromatography on silica (0-80% EtOAc/petroleum ether). LCMS (ES, m/z): 710.4 $[M+H]^+$. It was further purified by chiral SFC (Column DAICEL CHIRALCEL OD-H, 35% 0.1% $NH_3H_2O$ EtOH/$CO_2$) to give the title compound. $^1$H NMR (400 MHz, methanol-$d_4$): δ 8.32 (s, 1H), 8.28 (s, 1H), 7.84 (s, 1H), 7.79-7.57 (m, 3H), 7.51 (dd, J=3.1, 8.9 Hz, 1H), 7.43-7.37 (m, 1H), 7.37-7.30 (m, 2H), 4.95 (d, J=8.8 Hz, 1H), 3.74 (s, 3H), 2.24 (s, 3H), 2.18-2.02 (m, 3H), 1.55-1.32 (m, 2H), 1.27 (s, 3H), 1.14 (s, 3H), 0.94-0.74 (m, 1H).

Example 2

(R.Z)-5-(5-fluoro-2-(4-(trifluoromethyl)-1H-pyrazol-1-yl)phenyl)-2-(2⁴-((methoxycarbonyl)amino)-1⁵,5,5-trimethyl-4-oxo-1¹H-3-aza-1(4,2)-imidazola-2(1,2)-benzenacyclononaphane-9-yl)pyridine 1-oxide

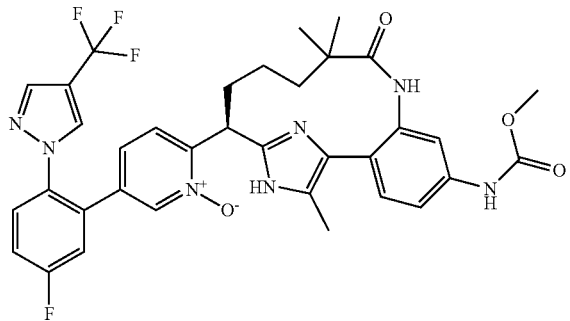 [SMILES: COC(=O)Nc1ccc2c(c1)NC(=O)C(C)(C)CCC[C@H](c1ccc(-c3cc(F)ccc3-n3cc(C(F)(F)F)cn3)c[n+]1[O-])c1nc-2c(C)[nH]1]

Step 1: 1-(4-fluoro-2-nitrophenyl)-4-(trifluoromethyl)-1H-pyrazole

To a stirred mixture of 4-(trifluoromethyl)-1H-pyrazole (3.85 g, 28.3 mmol), $Cs_2CO_3$ (20.48 g, 62.9 mmol) in DMF (100 mL) was added 1,4-difluoro-2-nitrobenzene (5 g, 31.4 mmol) at ambient temperature, and the reaction mixture was stirred at 25° C. for 1 h. Water (200 mL) was added, and the mixture was extracted with ethyl acetate (2×150 mL). The combined organic fractions were washed with water (2×100 mL) and brine (2×100 mL), dried over $Na_2SO_4$, filtered, and the solvent was evaporated under reduced pressure. The residue was purified by column chromatography on silica (0-10% EtOAc/petroleum ether) to give the title compound.

Step 2: 5-fluoro-2-(4-(trifluoromethyl)-1H-pyrazol-1-yl)aniline

To a stirred mixture of 1-(4-fluoro-2-nitrophenyl)-4-(trifluoromethyl)-1H-pyrazole (7.2 g, 26.2 mmol) in EtOAc (100 mL) was added Pd/C (4 g, 3.76 mmol) at ambient temperature, and the reaction mixture was stirred at 25° C. for 4 h under $H_2$ atmosphere. LCMS showed the reaction was completed. The mixture was filtered, and the filter cake was washed with ethyl acetate (100 mL). The filtrate was concentrated to dryness. The residue was used in next step without further purification. LCMS (ES, m/z): 245.9 $[M+H]^{30}$.

Step 3: 1-(2-bromo-4-fluorophenyl)-4-(trifluoromethyl)-1H-pyrazole

To a stirred mixture of 5-fluoro-2-(4-(trifluoromethyl)-1H-pyrazol-1-yl)aniline (8 g, 32.6 mmol), copper(II) bromide (0.729 g, 3.26 mmol), Tetrabutylammoniumbromide (21.04 g, 65.3 mmol), tosic acid (7.45 g, 39.2 mmol) in acetonitrile (200 mL) was added tert-butyl nitrite (4.04 g, 39.2 mmol) at 0° C., and the mixture was stirred at 25° C. for 1 h under $N_2$ atmosphere. LCMS showed the reaction was completed. Water (200 mL) was added, and the mixture was extracted with ethyl acetate (2×300 mL). The combined organic fractions were washed with brine (200 mL), dried over $Na_2SO_4$, filtered, and the solvent was evaporated under reduced pressure. The residue was purified by column chromatography on silica (petroleum ether:EtOAc=10:1) to give the title compound.

Step 4: methyl ((1²Z,8Z)-9-(5-(5-fluoro-2-(4-(trifluoromethyl)-1H-pyrazol-1-yl)phenyl)pyridin-2-yl)-1⁵,5,5-trimethyl-4-oxo-1¹-((2-(trimethylsilyl)ethoxy)methyl)-1¹H-3-aza-1(4,2)-imidazola-2(1,2)-benzenacyclononaphan-8-en-2⁴-yl)carbamate To a stirred mixture of (6-((1²Z,8Z)-2⁴-((methoxycarbonyl)amino)-1⁵,5,5-trimethyl-4-oxo-1¹-((2-(trimethylsilyl)ethoxy)methyl)-1¹H-3-aza-1(4,2)-imidazola-2(1,2)-benzenacyclononaphan-8-en-9-yl)pyridin-3-yl)boronic acid (9 g, 11.62 mmol), 1-(2-bromo-4-fluorophenyl)-4-(trifluoromethyl)-1H-pyrazole (3.95 g, 12.78 mmol), potassium phosphate (2 M in water, 17.43 mL, 34.9 mmol) in THF (200 mL) was added chloro[(di(1-adamantyl)-N-butylphosphine)-2-(2-aminobiphenyl)]palladium(II) (0.622 g, 0.930 mmol) at 25° C. under $N_2$, and the mixture was stirred at 80° C. for 3 h under $N_2$. LCMS showed that the reaction was completed. The mixture was cooled, diluted with ethyl acetate (200 mL), washed with brine (200 mL), dried over $Na_2SO_4$, filtered, and the solvent was evaporated under reduced pressure. The residue was purified by column chromatography on silica (0-35% EtOAc/petroleum ether) to give, the title compound. LCMS (ES, m/z): 804.5 $[M+H]^+$.

Step 5: methyl (R.Z)-(9-(5-(5-fluoro-2-(4-(trifluoromethyl)-1H-pyrazol-1-yl)phenyl)pyridin-2-yl)-1⁵,5,5-trimethyl-4-oxo-1¹-(2-trimethylsilyl)ethoxy)methyl)-1¹H-3-aza-1(4,2)-imidazola-2(1,2)-benzenacyclononaphane-2⁴-yl)carbamate To a stirred mixture of bis(norbornadiene)rhodium(I) tetrafluoroborate (0.456 g, 1.219 mmol) in 1,2-dichloroethane (15 mL) was added (S)-(+)-5,5'-bis[di(3,5-di-tert-butyl-4-methoxyphenyl)phosphino]-4,4'-bi-1,3-benzodioxole (1.541 g, 1.306 mmol) in a glove box at 25° C., and the mixture was stirred at 25° C. for 1 h. The mixture of methyl ((1²Z,8Z)-9-(5-(5-fluoro-2-(4-(trifluoromethyl)-1H-pyrazol-1-yl)phenyl)pyridin-2-yl)-1⁵,5,5-trimethyl-4-oxo-1¹-((2-(trimethylsilyl)ethoxy)methyl)-1¹H-3-aza-1(4,2)-imidazola-2(1,2)-benzenacyclononaphan-8-en-2⁴-yl)carbamate (14 g, 17.41 mmol) in 2,2,2-trifluoroethan-1-ol (150 mL) was added to the above mixture, and the mixture was stirred at 50° C. for 16 h under $H_2$. LCMS showed the reaction was completed. The mixture was concentrated. The residue was purified by column chromatography on silica (0-35% EtOAc/petroleum ether) to give the title compound. LCMS (ES, m/z): 806.5 $[M+H]^+$.

Step 6: (R.Z)-5-(5-fluoro-2-(4-(trifluoromethyl)-1H-pyrazol-1-yl)phenyl)-2-(2⁴-((methoxycarbonyl)amino)-1⁵,5,5-trimethyl-4-oxo-1¹-((2-(trimethylsilyl)ethoxy)methyl)-1¹H-3-aza-1(4,2)-imidazola-2(1,2)-benzenacyclononaphane-9-yl)pyridine 1-oxide To a stirred mixture of urea hydrogen peroxide (3.27 g, 34.7 mmol), sodium bicarbonate (5.84 g, 69.5 mmol) in dichloromethane (80 mL) was added trifluoroacetic anhydride (4.91 mL, 34.7 mmol) at 0° C., and the mixture was stirred at 0° C. for 5 min. Then methyl (R.Z)-(9-(5-(5-fluoro-2-(4-(trifluoromethyl)-1H-pyrazol-1-yl)phenyl)pyridin-2-yl)-1⁵,5,5-trimethyl-4-oxo-1¹-((2-(trimethylsilyl)ethoxy)methyl)-1¹H-3-aza-1(4,2)-imidazola-2(1,2)-benzenacyclononaphane-2⁴-yl)carbamate (7 g, 8.69 mmol)

in dichloromethane (20 mL) was added, and the mixture was stirred for 1 h. LCMS showed the reaction was completed. Water (100 mL) was added, and the mixture was extracted with dichloromethane (2×100 mL). The combined organic fractions were washed with aqueous $Na_2SO_3$ (20%, 100 mL) and brine (100 mL), dried over $Na_2SO_4$, filtered, and the solvent was evaporated under reduced pressure to afford the title compound which was used in next step without further purification. LCMS (ES, m/z): 822.5 $[M+H]^+$.

Step 7: (R,Z)-5-(5-fluoro-2-(4-(trifluoromethyl)-1H-pyrazol-1-yl)phenyl)-2-($2^4$-((methoxycarbonyl)amino)-$1^5$,5,5-trimethyl-4-oxo-$1^1$H-3-aza-1(4,2)-imidazola-2(1,2)-benzenacyclononaphane-9-yl) pyridine 1-oxide To a stirred mixture of (R,Z)-5-(5-fluoro-2-(4-(trifluoromethyl)-1H-pyrazol-1-yl)phenyl)-2-($2^4$-((methoxycarbonyl)amino)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphane-9-yl)pyridine 1-oxide (7 g, 8.52 mmol), (R)-2-amino-3-mercaptopropanoic acid (4.13 g, 34.1 mmol) in dichloromethane (50 mL) was added 2,2,2-trifluoroacetic acid (100 mL, 8.52 mmol) at ambient temperature, and the mixture was stirred at 40° C. for 4 h. LCMS showed the reaction was completed. The mixture was concentrated. The residue was diluted with ethyl acetate (200 mL), washed with aqueous sodium hydrogen carbonate (300 mL). The mixture was extracted with ethyl acetate (2×300 mL). The combined organic layers were dried over $Na_2SO_4$, filtered, and the solvent was evaporated under reduced pressure. The residue was purified by column chromatography on silica (0-80% EtOAc/petroleum ether). LCMS (ES, m/z): 692.4 $[M+H]^+$. It was purified again by chiral SFC (Column DAICEL CHIRALCEL OD, 45% 0.1% $NH_3H_2O$ MeOH/$CO_2$) to give the title compound. $^1$H NMR (400 MHz, methanol-$d_4$): δ 8.31 (s, 1H), 8.19 (s, 1H), 7.89 (s, 1H), 7.68-7.65 (m, 3H), 7.45-7.33 (m, 4H), 7.27 (d, J=8.3 Hz, 1H), 4.93 (d, J=9.3 Hz, 1H), 3.74 (s, 3H), 2.24 (s, 3H), 2.12 (s, 3H), 1.53-1.33 (m, 2H), 1.27 (s, 3H), 1.14 (s, 3H), 0.86 (br s, 1H).

Example 3

(R,Z)-5-(5-chloro-2-(4-(trifluoromethyl)-1H-pyrazol-1-yl)phenyl)-2-($2^4$-((methoxycarbonyl)amino)-$1^5$,5,5-trimethyl-4-oxo-$1^1$H-3-aza-1 4,2)-imidazola-2(1,2)-benzenacyclononaphane-9-yl)pyridine 1-oxide

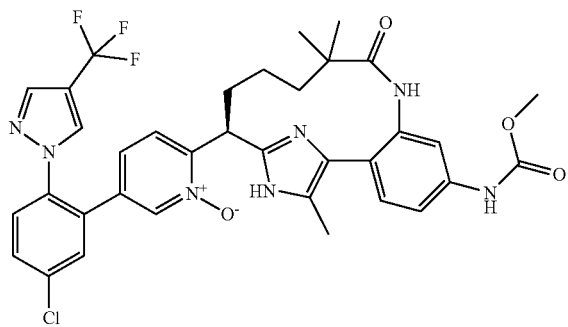 [SMILES: COC(=O)Nc1ccc2c(c1)NC(=O)C(C)(C)CCC[C@H](c1ccc(-c3cc(Cl)ccc3-n3cc(C(F)(F)F)cn3)c[n+]1[O-])c1nc-2c(C)[nH]1]

Step 1: 1-(2-bromo-4-chlorophenyl)-4-(trifluoromethyl)-1H-pyrazole

To a solution of 2-bromo-4-chloro-1-fluorobenzene (2093 mg, 9.99 mmol) and 4-(trifluoromethyl)-1H-pyrazole (800 mg, 5.88 mmol) in N,N-dimethylacetamide (10 mL) was added $Cs_2CO_3$ (3831 mg, 11.76 mmol). The mixture was heated to 80° C. for 12 h. LCMS showed the reaction was completed. The mixture was diluted with water (40 mL), extracted with EtOAc (60 mL×3). The combined organic layers were washed with water (30 mL) and brine (30 mL), dried over anhydrous sodium sulfate, filtered, and the filtrate was concentrated. The residue was purified by column chromatography on silica (100:1-5:1 petroleum ether:EtOAc) to give the title compound. LCMS (ES, m/z): 325.0, 326.9 $[M+H]^+$.

Step 2: (64($1^2$Z,8Z)-$2^4$-((methoxycarbonyl)amino)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphan-8-en-9-yl)pyridin-3-yl)boronic Acid To a mixture of methyl (($1^2$Z,8Z)-9-(5-chloropyridin-2-yl)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphan-8-en-$2^4$-yl)carbamate (4.8 g, 7.87 mmol) and 4,4,4',4',5,5,5',5'-octamethyl-2,2'-bi(1,3,2-dioxaborolane) (2.397 g, 9.44 mmol) in 1,4-dioxane (60 mL) were added X-Phos Pd G2, chloro(2-dicyclohexylphosphino-2',4',6'-triisopropyl-1,1'-biphenyl)[2-(2'-amino-1,1'-biphenyl)]palladium(II) (0.619 g, 0.787 mmol) and potassium acetate (1.544 g, 15.73 mmol) under $N_2$. The reaction mixture was stirred at 100° C. for 1.5 hours. LCMS showed the reaction was completed. Water (20 mL) was added and the mixture was extracted with ethyl acetate (2×100 mL). The combined organic fractions were washed with brine (3×100 mL), dried over $Na_2SO_4$, filtered, and the solvent was evaporated under reduced pressure to give the title compound. MS: 620.3 (M+1).

Step 3: methyl (($1^2$Z,8Z)-9-(5-(5-chloro-2-(4-(trifluoromethyl)-1H-pyrazol-1-yl)phenyl)pyridin-2-yl)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphan-8-en-$2^4$-yl)carbamate To a stirred mixture of (6-(($1^2$Z,8Z)-$2^4$-((methoxycarbonyl)amino)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphan-8-en-9-yl)pyridin-3-yl)boronic acid (300 mg, 0.428 mmol), 1-(2-bromo-4-chlorophenyl)-4-(trifluoromethyl)-1H-pyrazole (181 mg, 0.556 mmol), potassium phosphate (2 M in water, 0.428 mL, 0.855 mmol) in THF (4 mL) was added chloro[di(1-adamantyl)-N-butylphosphine)-2-(2-aminobiphenyl)]palladium (II) (28.6 mg, 0.043 mmol) in a glove box, and the mixture was stirred at 80° C. for 2 h under $N_2$ atmosphere. LCMS showed the reaction was completed. Water (10 mL) was added, and the mixture was extracted with ethyl acetate (2×20 mL). The combined organic fractions were washed with brine (2×30 mL), dried over $Na_2SO_4$, filtered, and the solvent was evaporated under reduced pressure. The residue was purified by column chromatography on silica (0-40% EtOAc/petroleum ether) to give the title compound. LCMS (ES, m/z): 820.3 $[M+H]^+$.

Step 4: methyl (R,Z)-(9-(5-(5-chloro-2-(4-(trifluoromethyl)-1H-pyrazol-1-yl)phenyl)pyridin-2-yl)-1⁵,5,5-trimethyl-4-oxo-1¹-((2-(trimethylsilyl)ethoxy)methyl)-1¹H-3-aza-1(4,2)-imidazola-2(1,2)-benzenacyclononaphane-2⁴-yl)carbamate To a stirred mixture of bis(norbornadiene)rhodium(I) tetrafluoroborate (8.02 mg, 0.021 mmol) in 1,2-dichloroethane (0.3 mL) was added (S)-(+)-5,5'-bis[di(3,5-di-tert-butyl-4-methoxyphenyl)phosphino]-4,4'-bi-1,3-benzodioxole (25.3 mg, 0.021 mmol) at ambient temperature in glove box. The reaction mixture was stirred at 25° C. for 1 h under N₂ atmosphere. A stirred mixture of methyl ((1²Z,8Z)-9-(5-(5-chloro-2-(4-(trifluoromethyl)-1H-pyrazol-1-yl)phenyl)pyridin-2-yl)-1⁵,5,5-trimethyl-4-oxo-1¹-((2-(trimethylsilyl)ethoxy)methyl)-1¹H-3-aza-1(4,2)-imidazola-2(1,2)-benzenacyclononaphan-8-en-2⁴-yl)carbamate (220 mg, 0.268 mmol) in 2,2,2-trifluoroethan-1-ol (10 mL) was added to the above catalyst mixture at ambient temperature, and the reaction mixture was stirred at 45° C. for 16 h under H₂ atmosphere (50 psi). LCMS showed the reaction was completed. The mixture was concentrated. The residue was purified by column chromatography on silica (0-40% EtOAc/petroleum ether) to give the title compound. LCMS (ES, m/z): 822.3 [M+H]⁺.

Step 5: (R,Z)-5-(5-chloro-2-(4-(trifluoromethyl)-1H-pyrazol-1-yl)phenyl)-2-(2⁴-((methoxycarbonyl)amino)-1⁵,5,5-trimethyl-4-oxo-1¹-((2-(trimethylsilyl)ethoxy)methyl)-1¹H-3-aza-1(4,2)-imidazola-2(1,2)-benzenacyclononaphane-9-yl)pyridine 1-oxide To a stirred mixture of urea hydrogen peroxide (80 mg, 0.851 mmol), sodium bicarbonate (143 mg, 1.702 mmol) in dichloromethane (5 mL) was added trifluoroacetic anhydride (0.120 mL, 0.851 mmol) at 25° C. and the mixture was stirred at 25° C. for 2 min under N₂ atmosphere. Then methyl (R,Z)-(9-(5-(5-chloro-2-(4-(trifluoromethyl)-1H-pyrazol-1-yl)phenyl)pyridin-2-yl)-1⁵,5,5-trimethyl-4-oxo-1¹-((2-(trimethylsilyl)ethoxy)methyl)-1¹H-3-aza-1(4,2)-imidazola-2(1,2)-benzenacyclononaphane-2⁴-yl)carbamate (140 mg, 0.170 mmol) in dichloromethane (2 mL) was added, and the mixture was stirred at 25° C. for 2 h. LCMS showed the reaction was completed. Water (10 mL) was added, and the mixture was extracted with dichloromethane (2×20 ml). The combined organic fractions were washed with aqueous Na₂SO₃ (10%, 50 mL) and brine (50 mL), dried over Na₂SO₄, filtered, and the solvent was evaporated under reduced pressure to give the title compound which was used in the next step directly. LCMS (ES, m/z): 838.5 [M+H]⁺.

Step 6: (R,Z)-5-(5-chloro-2-(4-(trifluoromethyl)-1H-pyrazol-1-yl)phenyl)-2-(2⁴-((methoxycarbonyl)amino)-1⁵,5,5-trimethyl-4-oxo-1¹H-3-aza-1(4,2)-imidazola-2(1,2)-benzenacyclononaphane-9-yl)pyridine 1-oxide To a stirred mixture of (R,Z)-5-(5-chloro-2-(4-(trifluoromethyl)-1H-pyrazol-1-yl)phenyl)-2-(2⁴-((methoxycarbonyl)amino)-1⁵,5,5-trimethyl-4-oxo-1¹-(2-(trimethylsilyl)ethoxy)methyl)-1¹H-3-aza-1(4,2)-imidazola-2(1,2)-benzenacyclononaphane-9-yl)pyridine 1-oxide (140 mg, 0.167 mmol), (R)-2-amino-3-mercaptopropanoic acid (101 mg, 0.835 mmol) in dichloromethane (4 mL) was added 2,2,2-trifluoroacetic acid (4 mL, 0.167 mmol), and the mixture was stirred at 40° C. for 2 h under N₂ atmosphere. The solvent was removed under reduced pressure, and the residue was purified by reverse phase HPLC (ACN/water with 0.1% TFA modifier). LCMS (ES, m/z): 708.4 [M+H]⁺. It was purified again by chiral SFC (Column DAICEL CHIRALCEL OD-H, 40% 0.1% NH₃H₂O EtOH/CO₂) to give the title compound. ¹H NMR (400 MHz, methanol-d₄): δ 8.33 (s, 1H), 8.18 (s, 1H), 7.89 (s, 1H), 7.75-7.56 (m, 5H), 7.42-7.37 (m, 1H), 7.36-7.32 (m, 1H), 7.26 (dd, J=1.3, 8.3 Hz, 1H), 4.93 (br d, J=10.1 Hz, 1H), 3.74 (s, 3H), 2.24 (s, 3H), 2.11 (br s, 3H), 1.52 (br s, 1H), 1.40 (br s, 1H), 1.27 (s, 3H), 1.14 (s, 3H), 0.84 (br s, 1H)

Example 4

(R,Z)-5-(5-chloro-2-(4-(difluoromethyl)-1H-pyrazol-1-yl)phenyl)-2-(2⁴-((methoxycarbonyl)amino)-1⁵,5,5-trimethyl-4-oxo-1¹H-3-aza-1(4,2)-imidazola-2(1,2)-benzenacyclononaphane-9-yl)pyridine 1-oxide

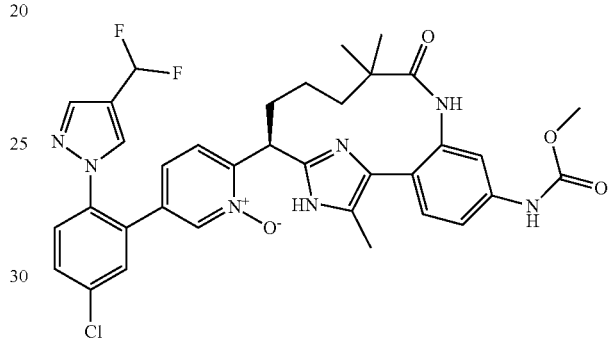

Step 1: 1-(2-bromo-4-chlorophenyl)-1H-pyrazole

To a mixture of 2-bromo-4-chloro-1-fluorobenzene (2 g, 9.55 mmol) and 1H-pyrazole (0.618 g, 9.07 mmol) in DMF (20 mL) was added Cs₂CO₃ (6.22 g, 19.10 mmol). The reaction mixture was stirred at 90° C. for 1 hour. LCMS showed the reaction was completed. The reaction was cooled to 25° C., diluted with EtOAc (30 mL) and water (30 mL). The aqueous layer was extracted with EtOAc (2×30 mL). The combined organic phase was dried over Na₂SO₄, filtered, and concentrated in vacuo. The residue was purified by, column chromatography on silica (0-10% EtOAc/petroleum ether) to give the title compound.

Step 2: 1-(2-bromo-4-chlorophenyl)-1H-pyrazole-4-carbaldehyde

To a mixture of 1-(2-bromo-4-chlorophenyl)-1H-pyrazole (1 g, 3.88 mmol) in 2,2,2-trifluoroacetic acid (10 mL) was added hexamethylenetetramine (0.708 g, 5.05 mmol). The reaction mixture was stirred at 100° C. for 16 hours. LCMS showed the reaction was completed. The reaction was cooled to 25° C., diluted with EtOAc (30 mL) and water (30 mL). The aqueous layer was extracted with EtOAc (2×30 mL). The combined organic phase was dried over Na₂SO₄, filtered, and concentrated in vacuo. The residue was purified by column chromatography on silica (0-30% EtOAc/petroleum ether) to give the title compound.

Step 3: 1-(2-bromo-4-chlorophenyl)-4-(difluoromethyl)-1H-pyrazole

To a mixture of 1-(2-bromo-4-chlorophenyl)-1H-pyrazole-4-carbaldehyde (200 mg, 0.700 mmol) in dichloromethane (8 mL) was added (diethylamino)sulfur trifluoride (DAST, 0.204 mL, 1.541 mmol). The reaction mixture was stirred at 40° C. for 16 hours. TLC showed the reaction was completed. The reaction mixture was cooled to 25° C., diluted with EtOAc (30 mL) and water (30 mL). The aqueous layer was extracted with EtOAc (2×30 mL). The combined organic phase was dried over $Na_2SO_4$, filtered, and concentrated in vacuo. The residue was purified by column chromatography on silica (0-10% EtOAc/petroleum ether) to give the title compound.

Step 4: methyl (($1^2Z,8Z$)-9-(5-(5-chloro-2-(4-(difluoromethyl)-1H-pyrazol-1-yl)phenyl)pyridin-2-yl)-$1^5$,5,5-trimethyl-4-oxo-$1^1$-(2-(trimethylsilyl)ethoxy)methyl)-$1^1$H-3-aza-1(4,2)-imidazola-2(1,2)-benzenacyclononaphan-8-en-$2^4$-yl)carbamate To a stirred mixture of (6-(($1^2Z,8Z$)-$2^4$-((methoxycarbonyl)amino)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphan-8-en-9-yl)pyridin-3-yl)boronic acid (280 mg, 0.452 mmol), 1-(2-bromo-4-chlorophenyl)-4-(difluoromethyl)-1H-pyrazole (139 mg, 0.452 mmol), potassium phosphate (1 M in water, 0.904 mL, 0.904 mmol) in THF (10 mL) was added chloro[(di(1-adamantyl)-N-butylphosphine)-2-(2-aminobiphenyl)]palladium (II) (30.2 mg, 0.045 mmol) and the mixture was stirred at 80° C. for 16 under $N_2$ atmosphere. LCMS showed the reaction was completed. Water (20 mL) was added, and the mixture was extracted with ethyl acetate (2×30 mL). The combined organic fractions were washed with brine (40 mL), dried over $Na_2SO_4$, filtered, and the solvent was evaporated under reduced pressure. The residue was purified by column chromatography on silica (0-50% EtOAc/petroleum ether) to give the title compound. LCMS (ES, m/z): 802.3 [M+H]$^+$.

Step 5: methyl (R.Z)-(9-(5-(5-chloro-2-(4-(trifluoromethyl)-1H-pyrazol-1-yl)phenyl)pyridin-2-yl)-$1^5$,5,5-trimethyl-4-oxo-$1^1$-((2-trimethylsilyl)ethoxy)methyl)-$1^1$H-3-aza-1(4,2)-imidazola-2(1,2)-benzenacyclononaphane-$2^4$-yl)carbamate To a stirred mixture of bis(norbornadiene)rhodium(I) tetrafluoroborate (19.11 mg, 0.051 mmol) in 1,2-dichloroethane (1 mL) was added (S)-(+)-5,5T-bis[di(3,5-di-tert-butyl-4-methoxyphenyl)phosphino]-4,4'-bi-1,3-benzodioxole (60.3 mg, 0.051 mmol) at ambient temperature in glove box, and the mixture was stirred at 25° C. for 1 h under $N_2$ atmosphere. A stirred mixture of methyl (($1^2Z,8Z$)-9-(5-(5-chloro-2-(4-(difluoromethyl)-1H-pyrazol-1-yl)phenyl)pyridin-2-yl)-$1^5$,5,5-trimethyl-4-oxo-$1^1$-((2-(trimethylsilyl)ethoxy)methyl)-1 $^1$H-3-aza-1(4,2)-imidazola-2(1,2)-benzenacyclononaphan-8-en-$2^4$-yl)carbamate (410 mg, 0.511 mmol) in 2,2,2-trifluoroethan-1-ol (2 mL) was added to the above catalyst mixture at ambient temperature, and the reaction mixture was stirred at 50° C. for 16 h under $H_2$ atmosphere (50 psi). LCMS showed the reaction was completed. Water (20 mL) was added, and the mixture was extracted with ethyl acetate (30 mL). The combined organic fractions were washed with brine (30 mL), dried over $Na_2SO_4$, filtered, and the solvent was evaporated under reduced pressure. The residue was purified by column chromatography on silica (0-50% EtOAc/petroleum ether) to give the title compound. LCMS (ES, m/z): 804 [M+H]$^+$.

Step 6: (R.Z)-5-(5-chloro-2-(4-(difluoromethyl)-1H-pyrazol-1-yl)phenyl)-2-($2^4$-((methoxycarbonyl)amino)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphane-9-yl)pyridine 1-oxide To a stirred mixture of methyl (R.Z)-(9-(5-(5-chloro-2-(4-(trifluoromethyl)-1H-pyrazol-1-yl)phenyl)pyridin-2-yl)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphane-$2^4$-yl)carbamate (265 mg, 0.329 mmol), urea hydrogen peroxide (155 mg, 1.647 mmol), sodium hydrogencarbonate (277 mg, 3.29 mmol) in dichloromethane (10 mL) was added 2,2,2-trifluoroacetic anhydride (346 mg, 1.647 mmol), and the mixture was stirred at 25° C. for 30 min. The mixture was poured into aqueous $Na_2SO_3$ (10 mL). The mixture was extracted with dichloromethane (2×15 mL), dried over $Na_2SO_4$ and filtered. The solvent was evaporated under reduced pressure. The mixture was purified by column chromatography on silica (0-80% EtOAc/petroleum ether) to give the title compound. LCMS (ES, m/z): 820.2 [M+H]$^+$.

Step 7: (R.Z)-5-(5-chloro-2-(4-(difluoromethyl)-1H-pyrazol-1-yl)phenyl)-2-($2^4$-((methoxycarbonyl)amino)-$1^5$,5,5-trimethyl-4-oxo-$1^1$H-3-aza-1(4,2)-imidazola-2(1,2)-benzenacyclononaphane-9-yl)pyridine 1-oxide A stirred mixture of (R.Z)-5-(5-chloro-2-(4-(difluoromethyl)-1H-pyrazol-1-yl)phenyl)-2-($2^4$-((methoxycarbonyl)amino)-$1^5$,5,5-trimethyl-4-oxo-$1^1$-((2-(trimethylsilyl)ethoxy)methyl)-$1^1$H-3-aza-1(4,2)-imidazola-2(1,2)-benzenacyclononaphane-9-yl)pyridine 1-oxide (210 mg, 0.256 mmol), (R)-2-amino-3-mercaptopropanoic acid (93 mg, 0.767 mmol) in 2,2,2-trifluoroacetic acid (4 mL, 51.9 mmol), dichloromethane (2 mL) was'stirred at 40° C. for 1 h. LCMS showed the reaction was completed. The mixture was concentrated. The residue was purified by column chromatography on silica (0-50% EtOAc/petroleum ether). LCMS (ES, m/z): 689.9 [M+H]$^+$. It was purified again by chiral SFC (Column DAICEL CHIRALPAK IC, 50% 0.1% $NH_3H_2O$ EtOH/$CO_2$). After concentration, 0.1% TFA/water solution was lyophilized to give the title compound as the TFA salt. $^1$H NMR (400 MHz, $CD_3OD$): δ 8.16 (d, J=1.3 Hz, 1H), 8.11 (s, 1H), 7.79-7.73 (m, 2H), 7.72-7.68 (m, 2H), 7.64-7.58 (m, 2H), 7.49-7.35 (m, 3H), 6.98-6.66 (m, 1H), 4.82 (br dd, J=6.6, 11.0 Hz, 1H), 3.77 (s, 3H), 2.32-2.16 (m, 5H), 1.81-1.68 (m, 1H), 1.59 (br s, 1H), 1.41-1.27 (m, 4H), 1.12 (s, 3H), 0.84 (br s, 1H).

Example 5

(R,Z)-5-(5-fluoro-2-(1-(trifluoromethyl)-1H-pyrazol-4-yl)phenyl)-2-(2⁴-((methoxycarbonyl)amino)-1⁵,5,5-trimethyl-4-oxo-1¹H-3-aza-1(4,2)-imidazola-2(1,2)-benzenacyclononaphane-9-yl)pyridine 1-oxide

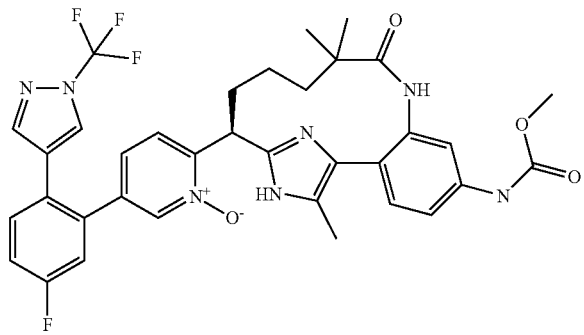 [SMILES: COC(=O)Nc1ccc2c(c1)NC(=O)C(C)(C)CCC[C@H](c1ccc(-c3cc(F)ccc3-c3cnn(C(F)(F)F)c3)c[n+]1[O-])c1nc-2c(C)[nH]1]

Step 1: 4-(2-chloro-4-fluorophenyl)-1-(trifluoromethyl)-1H-pyrazole

To a stirred mixture of 2-chloro-4-fluoro-1-iodobenzene (5.09 g, 19.84 mmol), 4-(4,4,5,5-tetramethyl-1,3,2-dioxaborolan-2-yl)-1-(trifluoromethyl)-1H-pyrazole (4 g, 15.27 mmol), $Na_2CO_3$ (4.85 g, 45.8 mmol) in DMF (30 mL) and water (10 mL) was added $Pd(dppf)Cl_2$ (1.117 g, 1.527 mmol) and the mixture was stirred at 80° C. for 2 h under $N_2$ atmosphere. LCMS showed the reaction was completed. Water (50 mL) was added and the mixture was extracted with ethyl acetate (2×00 mL). The combined organic fractions were washed with brine (2×100 mL), dried over $Na_2SO_4$, filtered, and the solvent was evaporated under reduced pressure. The residue was purified by column chromatography on silica (0-10% EtOAc/petroleum ether) to give the title compound. LCMS (ES, m/z): 265.0 [M+H]⁺.

Step 2: methyl((1²Z,8Z)-9-(5-(5-fluoro-2-(1-(trifluoromethyl)-1H-pyrazol-4-yl)phenyl)pyridin-2-yl)-1⁵,5,5-trimethyl-4-oxo-1¹-(2-(trimethylsilyl)ethoxy)methyl)-1¹H-3-aza-1(4,2)-imidazola-2(1,2)-benzenacyclononaphan-8-en-2⁴-yl)carbamate To a stirred mixture of (6-((1²Z,8Z)-2⁴-((methoxycarbonyl)amino)-1⁵,5,5-trimethyl-4-oxo-1¹-((2-(trimethylsilyl)ethoxy)methyl)-1¹H-3-aza-1-(4,2)-imidazola-2(1,2)-benzenacyclononaphan-8-en-9-yl)pyridin-3-yl)boronic acid (9.5 g, 10.73 mmol), 4-(2-chloro-4-fluorophenyl)-1-(trifluoromethyl)-1H-pyrazole (2.84 g, 10.73 mmol), potassium phosphate (2 M in water, 10.73 mL, 21.47 mmol) in THF (150 mL) was added chloro[(di(1-adamantyl)-N-butylphosphine)-2-(2-aminobiphenyl)]palladium (II) (0.718 g, 1.073 mmol), and the mixture was stirred at 80° C. for 2 h under $N_2$ atmosphere. LCMS showed the reaction was completed. Water (200 mL) was added, and the mixture was extracted with ethyl acetate (2×200 mL). The combined organic fractions were washed with brine (2×300 mL), dried over $Na_2SO_4$; filtered, and the solvent was evaporated under reduced pressure. The residue was purified by column chromatography on silica (0-40% EtOAc/petroleum ether) to give the title compound. LCMS (ES, m/z): 804.3 [M+H]⁺.

Step 3: methyl (R.Z)-(9-(5-(5-fluoro-2-(1-(trifluoromethyl)-1H-pyrazol-4-yl)phenyl)pyridin-2-yl)-1⁵,5,5-trimethyl-4-oxo-1¹-((2-trimethylsilyl)ethoxy)methyl)-1¹H-3-aza-1(4,2)-imidazola-2(1,2)-benzenacyclononaphane-2⁴-yl)carbamate To a stirred mixture of (S)-(+)-5,5"-bis[di(3,5-di-tert-butyl-4-methoxyphenyl)phosphino]-4,4'-bi-1,3-benzodioxole (0.873 g, 0.740 mmol) in 1,2-dichloroethane (0.3 mL) was added bis(norbornadiene)rhodium(I) tetrafluoroborate (0.277 g, 0.740 mmol) at ambient temperature in glove box, and the mixture was stirred at 25° C. for 1 h under $N_2$ atmosphere. A stirred mixture of methyl((1²Z,8Z)-9-(5-(5-fluoro-2-(1-(trifluoromethyl)-1H-pyrazol-4-yl)phenyl)pyridin-2-yl)-1⁵,5,5-trimethyl-4-oxo-1¹-((2-(trimethylsilyl)ethoxy)methyl)-1¹H-3-aza-1 (4,2)-imidazola-2(1,2)-benzenacyclononaphan-8-en-2⁴-yl)carbamate (8.5 g, 10.57 mmol) in 2,2,2-trifluoroethan-1-ol (5 mL) was added above catalyst mixture at room temperature and the mixture was stirred at 45° C. for 16 h under $H_2$ atmosphere (50 psi). LCMS showed the reaction was completed. The mixture was concentrated. The residue was purified by column chromatography on silica (0-40% EtOAc/petroleum ether) to give the title compound. LCMS (ES, m/z): 806.6 [M+H]⁺.

Step 4: (R.Z)-5-(5-fluoro-2-(1-(trifluoromethyl)-1H-pyrazol-4-yl)phenyl)-2-(2⁴-((methoxycarbonyl)amino)-1⁵,5,5-trimethyl-4-oxo-1¹-((2-(trimethylsilyl)ethoxy)methyl)-1¹H-3-aza-1(4,2)-imidazola-2(1,2)-benzenacyclononaphane-9-yl)pyridine 1-oxide To a stirred mixture of urea hydrogen peroxide (4.38 g, 46.5 mmol), sodium hydrogencarbonate (7.82 g, 93 mmol) in dichloromethane (3 mL) was added 2,2,2-trifluoroacetic anhydride (6.57 mL, 46.5 mmol) at 25° C. and the mixture was stirred at 25° C. for 2 min. Then methyl (R.Z)-(9-(5-(5-fluoro-2-(1-(trifluoromethyl)-1H-pyrazol-4-yl)phenyl)pyridin-2-yl)-1⁵,5,5-trimethyl-4-oxo-1¹-((2-(trimethylsilyl)ethoxy)methyl)-1¹H-3-aza-1(4,2)-imidazola-2(1,2)-benzenacyclononaphane-2⁴-yl)carbamate (7.5 g, 9.31 mmol) in dichloromethane (10 mL) was added, and the mixture was stirred at 25° C. for 2 h. LCMS showed the reaction was completed. Water (50 mL) was added, and the mixture was extracted with dichloromethane (2×60 mL). The combined organic fractions were washed with brine (2×50 mL), dried over $Na_2SO_4$, filtered, and the solvent was evaporated under reduced pressure to give the title compound which was used in the next step directly. LCMS (ES, m/z): 822.6 [M+H]⁺.

Step 5: (R.Z)-5-(5-fluoro-2-(1-(trifluoromethyl)-1H-pyrazol-4-yl)phenyl)-2-(2⁴-((methoxycarbonyl)amino)-1⁵,5,5-trimethyl-4-oxo-1¹H-3-aza-1(4,2)-imidazola-2(1,2)-benzenacyclononaphane-9-yl) pyridine 1-oxide To a stirred mixture of (R.Z)-5-(5-fluoro-2-(1-(trifluoromethyl)-1H-pyrazol-4-yl)phenyl)-2-(2⁴-((methoxycarbonyl)amino)-1⁵,5,5-trimethyl-4-oxo-1¹-((2-(trimethylsilyl)ethoxy)methyl)-1¹H-3-aza-1(4,2)-imidazola-2(1,2)-benzenacyclononaphane-9-yl)pyridine 1-oxide (8 g, 9.73 mmol), (R)-2-amino-3-mercaptopropanoic acid (5.90 g, 48.7 mmol) in dichloromethane (40 mL) was added 2,2,2-trifluoroacetic acid (40 mL, 9.73 mmol) and the mixture was stirred at 40° C. for 2 h. LCMS showed the reaction was completed. The solvent was removed under reduced pressure, and the residue was purified by column chromatography on silica (0-5% MeOH/dichloromethane). LCMS (ES, m/z): 692.4 [M+H]⁺. It was purified again by chiral SFC (Column DAICEL CHIRALCEL OD, 40% 0.1% NH$_3$H$_2$O EtOH/CO$_2$). The material was treated to CH$_3$CN (20 mL) and aqueous HCl (0.1%) and lyophilized to give the title compounds as the HCl salt. $^1$H NMR (500 MHz, methanol-d$_4$): δ 8.32 (s, 1H), 8.29 (s, 1H), 7.85 (d, J=8.2 Hz, 1H), 7.66-7.60 (m, 2H), 7.58 (br d, J=8.2 Hz, 1H), 7.53-7.49 (m, 2H), 7.48-7.44 (m, 1H), 7.35 (dt, J=2.6, 8.4 Hz, 1H), 7.30 (dd, J=2.7, 9.0 Hz, 1H), 4.95-4.94 (m, 1H), 3.79 (s, 3H), 2.38-2.23 (m, 5H), 1.88-1.76 (m, 1H), 1.70-1.58 (m, 1H), 1.46-1.33 (m, 4H), 1.14 (s, 3H), 1.00-0.57 (m, 1H).

Example 6

(R,Z)-5'-chloro-2'-(difluoromethoxy)-6-(2⁴-((methoxycarbonyl)amino)-1⁵, 5,5-trimethyl-4-oxo-1¹H-3-aza-1(4,2)-imidazola-2(1,2)- benzenacyclononaphane-9-yl)-[3,3'-bipyridine]1-oxide

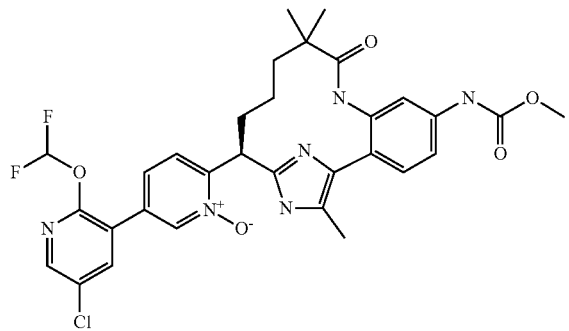 [SMILES: COC(=O)Nc1ccc2c(c1)NC(=O)C(C)(C)CCC[C@H](c1ccc(-c3cc(Cl)cnc3OC(F)F)c[n+]1[O-])c1nc-2c(C)[nH]1]

Step 1:
3-bromo-5-chloro-2-(difluoromethoxy)pyridine 2,2-difluoro-2-(fluorosulfonyl)acetic acid (1.581 g, 8.88 mmol) was added to a mixture of 3-bromo-5-chloropyridin-2-ol (1.85 g, 8.88 mmol) in MeCN (20 mL). The reaction mixture was stirred at 25° C. for 15 hours. The reaction mixture was diluted with EtOAc (20 mL) and water (20 mL). The aqueous layer was extracted with EtOAc (2×20 mL). The combined organic phase was dried over Na$_2$SO$_4$, filtered, and concentrated in vacuo. The residue was purified by flash silica gel chromatography (ISCO®; 20 g SepaFlash® Silica Flash Column, Eluent of 0-30% EtOAc/Pet. ether gradient @ 35 mL/min, dry loaded) to give the title compound.

Step 2: methyl ((1²Z,8Z)-9-(5¹-chloro-2'-(difluoromethoxy)-[3,3'-bipyridin]-6-yl)-1⁵,5,5-trimethyl-4-oxo-1¹-((2-(trimethylsilyl)ethoxy)methyl)-1¹H-3-aza-1(4,2)-imidazola-2(1,2)-benzenacyclononaphan-8-en-2⁴-yl)carbamate To a mixture of (6-((1²Z,8Z)-2⁴-((methoxycarbonyl)amino)-1⁵,5,5-trimethyl-4-oxo-1¹-((2-(trimethylsilyl)ethoxy)methyl)-1¹H-3-aza-1(4,2)-imidazola-2(1,2)-benzenacyclononaphan-8-en-9-yl)pyridin-3-yl)boronic acid (250 mg, 0.403 mmol) and 3-bromo-5-chloro-2-(difluoromethoxy)pyridine (125 mg, 0.484 mmol) in 1,4-dioxane (10.0 mL) were added Pd(dppf)Cl$_2$ (35.4 mg, 0.048 mmol) and K$_3$PO$_4$ (0.605 mL, 1.210 mmol) under N$_2$. The reaction mixture was stirred at 80° C. for 5 hours. The reaction mixture was then cooled to 25° C., and diluted with EtOAc (20 mL) and water (20 mL). The aqueous layer was extracted with EtOAc (2×20 mL). The combined organic phase was dried over Na$_2$SO$_4$, filtered, and concentrated in vacuo. The residue was purified by flash silica gel, chromatography (ISCO®; 12 g SepaFlash® Silica Flash Column, Eluent of 20~40% EtOAc/Pet. ether gradient @ 30 mL/min) to give the title compound. LCMS (ES, m/z): 753.2 [M+H]⁺.

Step 3: methyl (R,Z)-(9-(5'-chloro-2'-(difluoro methoxy)-[3,3'-bipyridin]-6-yl)-1⁵,5,5-trimethyl-4-oxo-1¹-((2-(trimethylsilyl)ethoxy)methyl)- 1¹H-3-aza-1(4,2)-imidazola-2(1,2)-benzene cyclononaphane-2⁴-yl)carbamate (S)-(+)-5,5'-bis(bis(3,5-di-tert-butyl-4-methoxy phenyl) phosphino)-4,4'-bibenzo[d][1,3]dioxole (43.8 mg, 0.037 mmol) was added to a stirred mixture of bis(norbornadiene) rhodium(I)tetrafluoroborate (13.90 mg, 0.037 mmol) in DCE (1.0 mL) at 25° C. in glove box and the mixture was stirred at 25° C. for 1 hour under N$_2$. The above mixture was added to a mixture of methyl ((1²Z,8Z)-9-(5'-chloro-2'-(difluoromethoxy)-[3,3'-bipyridin]-6-yl)-1⁵,5,5-trimethyl-4-oxo-1¹-((2-trimethylsilyl)ethoxy)methyl)-1¹H-3-aza-1(4,2)-imidazola-2(1,2)-benzenacyclononaphan-8-en-2⁴-yl) carbamate (280 mg, 0.372 mmol) in 2,2,2-trifluoroethan-1-ol (8.0 mL) under N$_2$. The suspension was degassed under vacuum and purged with H$_2$ several times. The mixture was stirred under H$_2$ (50 psi) at 50° C. for 24 hours. The reaction mixture was then cooled to 25° C. The suspension was filtered through a pad of celite and the filter cake was washed with DCM (10 mL×2). The combined filtrates were concentrated to dryness. The residue was purified by flash silica gel chromatography (ISCO®; 12 g SepaFlash® Silica Flash Column, Eluent of 20-50% EtOAc/Pet. ether gradient @ 30 mL/min) to afford the title compound. LCMS (ES, m/z): 755.2[M+H]⁺.

Step 4: (R,Z)-5'-chloro-2'-(difluoromethoxy)-6-(2⁴-((methoxycarbonyl)amino)-1⁵,5,5-trimethyl-4-oxo-1¹-((2-(trimethylsilyl)ethoxy)methyl)-1¹H-3-aza-1(4,2)-imidazola-2(1,2)-benzenacyclononaphane-9-yl)-[3,3'-bipyridine]1-oxide To a mixture of H$_2$O$_2$·Urea (131 mg, 1.390 mmol) and NaHCO$_3$ (234 mg, 2.78 mmol) in DCM (5.0 mL) was added dropwise 2,2,2-trifluoroacetic anhydride (0.193 mL, 1.390 mmol). The reaction mixture was stirred at 0° C. for 5 mins. Methyl (R,Z)-(9-(5'-chloro-2'-(difluoro methoxy)-[3,3'-bipyridin]-6-yl)-1⁵,5,5-trimethyl-4-oxo-1¹-((2-(trimethylsilyl) ethoxy)methyl)-1¹H-3-aza-1(4,2)-imidazola-2(1,2)- benzenacyclononaphane-2⁴-yl)carbamate (210 mg, 0.278 mmol) in DCM (2.0 mL) was added dropwise to the above mixture. The resulting mixture was stirred at 25° C. for 40 mins. The reaction mixture was quenched with 15 mL of saturated aqueous Na$_2$SO$_3$. The resulting solution was extracted with DCM (2×10 mL). The combined organic phase was dried over Na$_2$SO$_4$, filtered, and concentrated in vacuo to afford the title compound which was used directly for the next step without further purification. LCMS (ES, m/z): 771.2[M+H]⁺.

Step 5: (R,Z)-5'-chloro-2'-(difluoromethoxy)-6-(2⁴-((methoxycarbonyl)amino)-1⁵,5,5-trimethyl-4-oxo-1¹H-3-aza-1(4,2)-imidazola-2(1,2)-benzenacyclononaphane-9-yl)-[3,3'-bipyridine]1-oxide To a mixture of (R,Z)-5'-chloro-2'-(difluoromethoxy)-6-(2⁴-((methoxycarbonyl)amino)-1⁵,5,5-trimethyl-4-oxo-1¹-

((2-(trimethylsilyl)ethoxy)methyl)-1$^1$H-3-aza-1(4,2)-imidazola-2(1,2)-benzenacyclononaphane-9-yl)-[3,3'-bipyridine] 1-oxide (210 mg, 0.272 mmol) in a mixture of DCM (2.0 mL) and TFA (4.0 mL) was added DL-cysteine (99 mg, 0.817 mmol). The reaction mixture was stirred at 40° C. for 2 hours. The reaction mixture was concentrated in vacuo and the residue purified by reverse phase HPLC (ACN/water with 0.1% TFA modifier) to afford the title compound as the TFA salt. LCMS (ES, m/z): 641.0 [M+H]$^+$. $^1$H NMR (methanol-d4, 500 MHz) δ 8.65 (s, 1H), 8.33 (d, J=2.4 Hz, 1H), 8.14 (d, J=2.4 Hz, 1H), 7.96-7.87 (m, 2H), 7.65 (t, J=72.0 Hz, 1H), 7.63 (s, 2H), 7.41-7.35 (m, 1H), 4.88-4.80 (m, 1H), 3.75 (s, 3H), 2.32-2.12 (m, 5H), 1.82-1.47 (m, 2H), 1.37-1.18 (m, 4H), 1.16-0.83 (m, 4H).

Factor XIa Assay

The effectiveness of a compound of the present invention as an inhibitor of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the half-maximal inhibitory concentrations (IC50), or the inhibitory constant, $K_i$.

Compounds were pre-incubated for 30 minutes at 25° C. with human (0.04 nM) Factor XIa in 50 mM HEPES buffer with 150 mM sodium chloride, 5 mM calcium chloride, 0.1% PEG 8000, pH 7.4. Factor XIa enzymatic activity was determined by addition of the substrate glycine-proline-arginine-7-amido-4-trifluoromethylcoumarin (GPR-AFC) and measurement of the fluorescence at 400/505 nm after a 60 minute incubation at 25° C. The % inhibition for each data point was calculated from the data and analyzed using the log (inhibitor) vs. response four parameters equation to determine the half-maximal inhibitory concentrations (IC50). The IC50 were, converted to equilibrium inhibitory constants (Ki) using the Cheng-Prusoff equation.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Kallikrein Assay

The effectiveness of a compound of the present invention as an inhibitor of Kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the half-maximal inhibitory concentrations (IC50), or the inhibitory constant, Kallikrein determinations were made in 50 mM HEPES buffer at pH 7.4 containing 150 mM NaCl, 5 mM $CaCl_2$, and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K—P—R-AFC (Sigma #C6608) at a concentration of 100 mM.

Activity assays were performed by diluting a stock solution of substrate at least tenfold to a final concentration ≤0.2 Km into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). IC50 was determined by inflection point from a four parameter logistic curve fit. Ki was calculated using the Cheng Prusoff equation, $Ki=IC_{50}/(1+([S]/Km))$.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Activated Partial Thromboplastin Time (aPTT) Assay

Activated partial thromboplastin time (aPTT) is a clotting test that measures the intrinsic coagulation cascade. The test is performed in sodium citrated plasma. Human plasma is made by collecting blood from healthy donors of both genders into Na citrate tubes (Sarstedt coagulation 9NC/10 ml). Blood is centrifuged at 1500×g and the plasma is collected. aPTT is checked on each individual donor, and those within the normal range (28-40 seconds) are pooled, aliquoted, and stored at −80° C. Test samples are prepared by spiking inhibitors or vehicle into plasma. These spiked samples are then run on a coagulation analyzer (STA-R Evolution, Stago Diagnostica). In general, the analyzer performs the following steps: Factor XII is activated by addition of ellagic acid (Pacific Hemostasis), and then time to clot is measured after re-calcification of the sample. Inhibition of FXI will cause aPTT clot time to be prolonged. The data are expressed as percent increase over vehicle control clot time and the concentration that causes a 50% (1.5×) percent increase of clot time.

Norepinephrine Transporter Binding Assay

Human Norepinephrine Transporter (NET) Binding (Antagonist Radioligand) was determined at Panlabs Cerep (assay #204410). Human norepinephrine transporters expressed in dog kidney MDCK cells were used in modified Tris-HCl buffer pH 7.4. A 40 µg‡ aliquot was incubated with 0.2 nM [125I]RTI-55 for 3 hours at 4° C. Non-specific binding was estimated in the presence of 10 µml desipramine. Membranes were filtered and washed, and the filters were then counted to determine [125I]RTI-55 specifically bound. Compounds were assayed using an 8-point titration, with a starting concentration of 10 µM and one-half log serial dilutions. ‡Note: Membrane protein may change from lot to lot, the concentration used is adjusted if necessary. IC50 values were determined by a non-linear, least squares regression analysis using MathIQ™ (IDBusiness Solutions Ltd., UK).

Norepinephrine Transporter Functional Antagonist Uptake Assay

Human Norepinephrine Transporter (NET) Functional Antagonist Uptake Assay was carried out at Panlabs Cerep (assay #302100). Human recombinant norepinephrine transporter expressed in MDCK cells were plated overnight. Test compound and/or vehicle was pre-incubated with cells (2×10E5/ml) in modified Tris-HEPES buffer pH 7.1 for 20 minutes at 25° C. and 25 nM [3H]Norepinephrine was then added for an additional 15 minute incubation period. A lysate was obtained from solubilized cells and counted to determine [3H]Norepinephrine uptake. Reduction of [3H]Norepinephrine uptake by 50 percent or more (≥50%) relative to 10 µM desipramine indicates significant inhibitory activity. Compounds are screened at 10, 3, 1, 0.3, 0.1, 0.03, 0.01 and 0.003 µM. These same concentrations are concurrently applied to a separate group of untreated cells and evaluated for possible compound-induced cytotoxicity only if significant inhibition of uptake is observed. IC50 values were determined by a non-linear, least squares regression analysis using MathIQ™ (IDBusiness Solutions Ltd., UK).

Inhibition of Tissue Kallikrein Enzymatic Activity

Compounds were assayed with human tissue kallikrein (RayBiotech, Cat #228-10996 or Evotec, final concentration 5 nM) in 50 mM HEPES, 150 mM NaCl, 5 mM CaCl$_2$, 0.1% PEG pH 7.4 at 25° C. in a Corning 3575 non-binding surface microplate. Compounds were tested in 10-point dose titrations starting at 166.67 uM with a 3-fold dilution series. Tissue kallikrein enzymatic activity was determined by measuring the rate of cleavage of N-acetyl-KPR-AFC substrate (Sigma, Cat #C6608, final concentration 100 uM) by continuously monitoring the fluorescence at 400/505 nm using a Tecan Safire plate-reader. The initial reaction rates (0 to 20 minutes) were used to determine percent inhibition. The % Inhibition for each data point was recalculated from the RFU/min data and analyzed using the log(inhibitor) vs. response four parameters equation with the GraphPad Prism software.

High-Throughput (HT) Solubility Determination

The chromatographic system consists of an Agilent 1290 UPLC/DAD system and ChemStation software, both from Agilent Technologies, USA. The separations are carried out on a Supelco Ascentis Express C18, 30 mm×3.0 mm I.D., 2.7 µm HPLC column. The mobile phase consists of Potassium phosphate buffered at pH 7 (mobile phase A) and acetonitrile (mobile phase B). The column oven temperature is set to 30° C. and the UPLC analysis consists of a gradient. The injection volume is 2 µL and the spectrophotometric detection is set to 215 and 238 nm.

A 10 mM stock solution of the compound in DMSO is supplied for analysis. 2.5 µL of stock solution (10 mM) was diluted into 247.5 µL of organic co-solvents (10% MeCN/80% MeOH/10% DMSO, v/v/v) to create a standard solution of 100 µM. To create the solubility solutions, 4.1 µL of 10 mM DMSO stock solution was diluted into 247.5 µL of phosphate buffered saline (PBS) (pH 7) solution. A second 4.1 µL aliquot of 10 mM DMSO stock solution was added to 196 µL of PBS (pH 2) solution. A third 4.1 µL aliquot of 10 mM DMSO stock solution was added to 196 µL of FaSSIF (pH 6.5) solution. Each solubility solution was sealed and shaken for 24 hours at 25° C. Filtered the equilibrated solubility solutions by centrifugation using a filter (0.45 µm, polypropylene). Placed 50 µL each of the 100 µM standard solution and the filtered equilibrated solubility solutions into a 384 well plate, and the plate was subsequently heat sealed.

Analyzed each standard and solubility solution by UPLC/DAD. The solubility value was calculated by the following equation:

Solubility=(Peak area of sample/Peak area of standard)(Standard concentration)

The following table shows representative data for the compounds of the Examples. In this table, the FXIa Ki is a measure of the ability of the test compound to inhibit the action of the FXIa enzyme. Such results are indicative of the intrinsic activity of the compounds for use as inhibitors of the FXIa enzyme. Additionally Plasma Kallikrein (pKal) inhibition, tissue Kallikrein inhibition (tKal) and Norepinephrine Transporter functional antagonist uptake activity (NET) are provided.

TABLE 1

| Example | FXIa IC$_{50}$ (nM) | pKal IC$_{50}$ (nM) | tKal IC$_{50}$ (nM) | NET IC$_{50}$ (nM) |
|---|---|---|---|---|
| 1 | 1.5 | 480 | >167,000 | >10,000 |
| 2 | 2.9 | 1080 | 90,000 | >10,000 |
| 3 | 0.89 | 42 | >167,000 | >10,000 |
| 4 | 0.90 | 46 | >167,000 | 6,500 |
| 5 | 2.0 | 371 | >167,000 | >10,000 |
| 6 | 4.4 | 443 | | 180 |

Pharmacokinetic General Procedures:

Rat Cassette Generic Procedure

Plasma pharmacokinetic parameters for clearance, volume of distribution, half-life and mean residence time (MRT) were determined in rats from IV cassette administration studies. 2 male rats typically weighing 225-260 gram, were fasted overnight prior to dosing. Compounds were prepared for IV dosing by addition to a vehicle, depending on the dose used. For a typical preparation, 1 mg per mL (IV) of up to 5 test compounds were added to vehicle comprised of 20% dimethyl sulfoxide (DMSO), 60% polyethylene glycol 400 (PEG400) and 20% water. IV formulation was administered to 2 rats via pre-cannulated jugular vein. Blood was collected by pre-cannulated artery, typically at predose, 2, 8, 15, 30 min, 1, 2, 4, 6, and 8 hr postdose. Samples were collected in K2EDTA tubes, stored on ice, and centrifuged. Plasma was transferred to a micro titer plate and stored at −70° C. until analysis. Plasma samples were extracted using protein precipitation and analyzed by liquid chromatography separation followed by mass spec detection (LCMS/MS), using a standard curve for each compound. Plasma pharmacokinetic parameters were calculated by non-compartmental methods.

Rat Screening IV/PO Generic Procedure

Plasma pharmacokinetic parameters for clearance, volume of distribution, half-life, mean residence time (MRT) and oral bioavailability (% F)—were determined in rats from oral administration and IV administration studies. 4 male rats, typically weighing 225-260 gram, were fasted overnight prior to dosing. Compounds were prepared for oral and IV dosing by addition to a vehicle, depending on the dose used. For a typical preparation, 1 mg per mL (IV) or 1.5 mg per mL (oral) of test compound was added to vehicle comprised of 20% dimethyl sulfoxide (DMSO), 60% polyethylene glycol 400 (PEG400) and 20% water. IV formulation was administered to 2 rats via pre-cannulated jugular vein, and oral dosing was administered to 2 rats via oral gavage. Blood was collected by pre-cannulated artery, typically at predose, 2 min, 8 min, 15 min, 30 min, and 1, 2, 4, 6, and 8 hr postdose for IV, and at predose, 15 min, 30 min, and 1, 2, 4, 6, 8 hr for oral dosing. Samples were collected in K2EDTA tubes, stored on ice, and centrifuged. Plasma was transferred to a micro titer plate and stored at −70° C. until analysis. Plasma samples were extracted using protein precipitation and analyzed by liquid chromatography separation followed by mass spec detection (LCMS/MS), using a standard curve for each compound. Plasma pharmacokinetic parameters were calculated for IV and oral dosing data by non-compartmental methods. Oral bioavailability was determined as the ratio of the dose-normalized plasma area under the curve (AUC) following oral dosing vs. IV dosing.

Dog Screening IV/PO Generic Procedure

Plasma pharmacokinetic parameters for clearance, volume of distribution, half-life, mean residence time (MRT) and oral bioavailability were determined in dogs from oral administration and IV administration studies. 4 male dogs, typically weighing 8-12 kilograms, were fasted overnight prior to dosing. Compounds were prepared for oral and IV dosing by addition to a vehicle, depending on the dose used. For a typical preparation, 1 mg per mL (IV) or 1.5 mg per mL (oral) of test compound was added to vehicle comprised of 20% dimethyl sulfoxide (DMSO), 60% polyethylene glycol 400 (PEG400) and 20% water. IV formulation was administered to 2 dogs via the saphenous or cephalic vein, and oral dosing was administered to 2 dogs via oral gavage. Blood was collected by the cephalic or jugular vein, typically at predose, 2 min, 8 min, 15 min, 30 min, and 1, 2, 4, 6, 8 and 24 hr postdose for IV, and at predose, 15 min, 30 min, and 1, 2, 4, 6, 8, and 24 hr for oral dosing. Samples were collected in K2EDTA tubes, stored on ice, and centrifuged. Plasma was transferred to a micro titer plate and stored at −70° C. until analysis. Plasma samples were extracted using protein precipitation and analyzed by liquid chromatography separation followed by mass spec detection (LCMS/MS), using a standard curve for each compound. Plasma pharmacokinetic parameters were calculated for IV and oral dosing data by non-compartmental methods. Oral bioavailability was determined as the ratio of the dose-normalized plasma area under the curve (AUC) following oral dosing vs. IV dosing.

Dog Cassette Generic Procedure

Plasma pharmacokinetic parameters for clearance, volume of distribution, half-life, and mean residence time (MRT) were determined in dogs from IV cassette administration studies. 2 male dogs, typically weighing 8-12 kilograms, were fasted overnight prior to dosing. Compounds were prepared for IV dosing by addition to a vehicle, depending on the dose used. For a typical preparation, 1 mg per mL (IV) of up to 5 test compounds were added to vehicle comprised of 20% dimethyl sulfoxide (DMSO), 60% polyethylene glycol 400 (PEG400) and 20% water. IV formulation was administered to 2 dogs via the saphenous or cephalic vein. Blood was collected by the cephalic or jugular vein, typically at predose, 2, 8, 15, 30 min, 1, 2, 4, 6, 8 and 24 hr postdose. Samples were collected in K2EDTA tubes, stored on ice, and centrifuged. Plasma was transferred to a micro titer plate and stored at −70° C. until analysis. Plasma samples were extracted using protein precipitation and analyzed by liquid chromatography separation followed by mass spec detection (LCMS/MS), using a standard curve for each compound. Plasma pharmacokinetic parameters were calculated by non-compartmental methods.

TABLE 2

| Example | Rat MRT (h) | Dog MRT (h) | pH 2 solubility (µM) | pH 6.5 (FaSSIF) solubility (µM) |
|---|---|---|---|---|
| 1 | 5.8 | 10 | >200 | 36 |
| 2 | 5.7 | 11 | 209 | 53 |
| 3 | 11 | 10* | 159 | 27 |
| 4 | 2.7 | 8.7 | 166 | 44 |
| 5 | 4.5 | 10 | 146 | 50 |
| 6 | 5.6 | 14.5 | 143 | 55 |

*cassette IV procedure; all others used IV/PO procedure

The following table shows representative data for the compounds of the Examples. In this table, select pharmacokinetic data (MRT=mean residence time) for both rat and dog are provided. Additionally the high-throughput solubility in pH2 phosphate buffer solution (PBS) and pH6.5 FaSSIF (Fasted State Simulated Intestinal Fluid) is provided.

What is claimed is:

1. A compound of the formula:

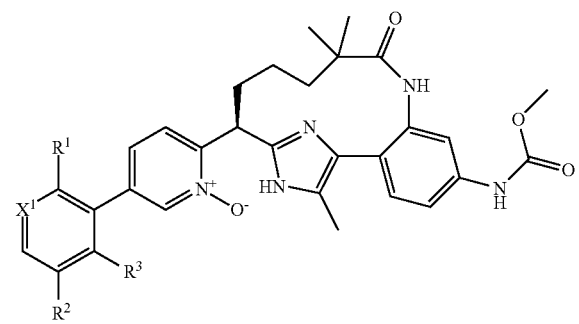

wherein $R^1$ is OCHF$_2$ when $X^1$ is N, or $R^1$ is a pyrazole optionally substituted with $R^4$ when $X^1$ is CH;

$R^2$ is chloro or fluoro;

$R^3$ is hydrogen or fluoro;

$R^4$ is CHF$_2$ or CF$_3$;

$X^1$ is CH or N;

or a pharmaceutically acceptable salt thereof.

2. The compound of claim 1 of the formula:

wherein
R² is chloro or fluoro;
R³ is hydrogen or fluoro;
R⁴ is CHF₂ or CF₃;
R⁵ is a pyrazole optionally substituted with R⁴;
or a pharmaceutically acceptable salt thereof.

3. The compound of claim 1 of the formula:

wherein
R² is chloro or fluoro;
R³ is hydrogen or fluoro;
R⁴ is CHF₂ or CF₃;
or a pharmaceutically acceptable salt thereof.

4. The compound of claim 1 of the formula:

wherein
R² is chloro or fluoro;
R³ is hydrogen or fluoro;
R⁴ is CHF₂ or CF₃;
or a pharmaceutically acceptable salt thereof.

5. The compound of claim 1 of the formula:

wherein
R² is chloro;
R³ is hydrogen;
or a pharmaceutically acceptable salt thereof.

6. The compound of claim 1 wherein X¹ is CH; or a pharmaceutically acceptable salt thereof.

7. The compound of claim 1 wherein X¹ is N; or a pharmaceutically acceptable salt thereof.

8. The compound of claim 1 wherein R¹ is OCHF₂; or a pharmaceutically acceptable salt thereof.

9. The compound of claim 1 wherein R¹ is pyrazole optionally substituted with R⁴; or a pharmaceutically acceptable salt thereof.

10. The compound of claim 1 wherein R² is fluoro; or a pharmaceutically acceptable salt thereof.

11. The compound of claim 1 wherein R² is chloro; or a pharmaceutically acceptable salt thereof.

12. The compound of claim 1 wherein R³ is hydrogen; or a pharmaceutically acceptable salt thereof.

13. The compound of claim 1 wherein R³ is fluoro; or a pharmaceutically acceptable salt thereof.

14. The compound of claim 1 wherein R⁴ is CHF₂; or a pharmaceutically acceptable salt thereof.

15. The compound of claim 1 wherein R⁴ is CF₃; or a pharmaceutically acceptable salt thereof.

16. The compound of claim 1 selected from:

-continued
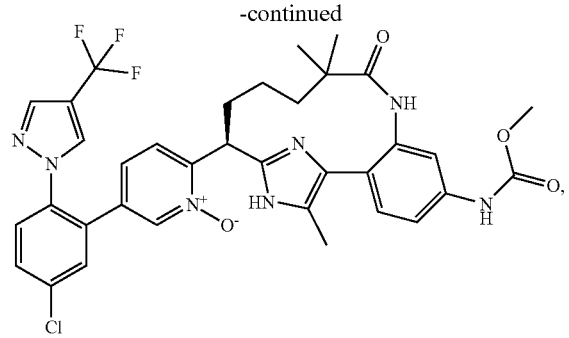
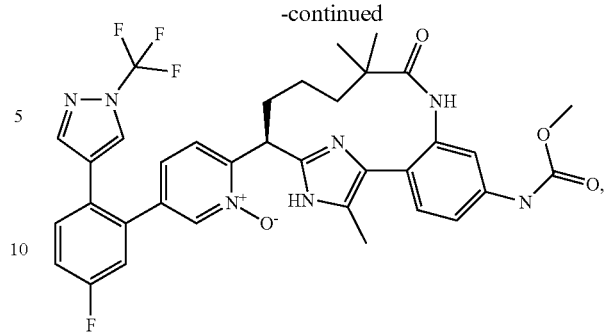
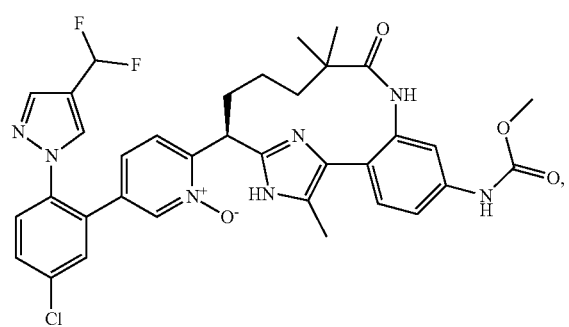
or a pharmaceutically acceptable salt thereof.
17. A pharmaceutical composition comprising a compound of claim 1 or a pharmaceutically acceptable salt thereof and a pharmaceutically acceptable carrier.
* * * * *